(12) United States Patent
Zopf et al.

(10) Patent No.: US 11,564,792 B2
(45) Date of Patent: Jan. 31, 2023

(54) EAR TISSUE SCAFFOLD IMPLANT FOR AURICULAR TISSUE RECONSTRUCTION

(71) Applicant: THE REGENTS OF THE UNIVERSITY OF MICHIGAN, Ann Arbor, MI (US)

(72) Inventors: David A. Zopf, Dexter, MI (US); Scott J. Hollister, Atlanta, GA (US)

(73) Assignee: THE REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 86 days.

(21) Appl. No.: 16/608,716

(22) PCT Filed: Apr. 26, 2018

(86) PCT No.: PCT/US2018/029575
§ 371 (c)(1),
(2) Date: Oct. 25, 2019

(87) PCT Pub. No.: WO2018/200816
PCT Pub. Date: Nov. 1, 2018

(65) Prior Publication Data
US 2020/0188090 A1 Jun. 18, 2020

Related U.S. Application Data

(60) Provisional application No. 62/490,312, filed on Apr. 26, 2017.

(51) Int. Cl.
*A61F 2/18* (2006.01)
*A61F 2/00* (2006.01)
(Continued)

(52) U.S. Cl.
CPC .............. *A61F 2/18* (2013.01); *A61F 2/0059* (2013.01); *B33Y 70/00* (2014.12);
(Continued)

(58) Field of Classification Search
CPC combination set(s) only.
See application file for complete search history.

(56) References Cited

U.S. PATENT DOCUMENTS

| | | | |
|---|---|---|---|
| 4,595,713 A | 6/1986 | St. John | |
| 5,433,748 A * | 7/1995 | Wellisz | ..................... A61F 2/18 |
| | | | 623/10 |

(Continued)

FOREIGN PATENT DOCUMENTS

| CN | 203183985 U | 9/2013 |
|---|---|---|
| CN | 104783922 A | 7/2015 |

(Continued)

OTHER PUBLICATIONS

Extended European Search Report for European Patent Application No. 18789867.1 dated Dec. 14, 2020, 8 pages.

(Continued)

*Primary Examiner* — Yashita Sharma
(74) *Attorney, Agent, or Firm* — Harness, Dickey & Pierce, P.L.C.

(57) ABSTRACT

Ear implants for auricular tissue reconstruction in a patient are provided. The ear implant may be a tissue scaffold multicomponent assembly for reconstruction of auricular tissue. Thus, the assembly may include both a first and a second tissue scaffold component. Each comprises a biocompatible polymeric material having a plurality of open pores configured to support cell growth. The first tissue scaffold component defines a central void region and at least a portion of an outer ear framework of the patient after implantation. The second tissue scaffold component defines a base portion. After implantation into the patient, the second tissue scaffold component seats within the central void region of the first tissue scaffold component, so that the second tissue scaffold component is secured to the first tissue (Continued)

scaffold component. Methods for reconstructing auricular tissue in a patient using such ear implant tissue scaffolds are also provided.

21 Claims, 14 Drawing Sheets

(51) Int. Cl.
    *B33Y 70/00*     (2020.01)
    *A61L 27/18*     (2006.01)
    *A61L 27/36*     (2006.01)
    *A61L 27/56*     (2006.01)
    *A61L 27/58*     (2006.01)

(52) U.S. Cl.
    CPC ......... *A61F 2002/183* (2013.01); *A61L 27/18* (2013.01); *A61L 27/362* (2013.01); *A61L 27/56* (2013.01); *A61L 27/58* (2013.01); *A61L 2430/14* (2013.01)

(56) References Cited

U.S. PATENT DOCUMENTS

| | | | |
|---|---|---|---|
| 6,187,329 B1 * | 2/2001 | Agrawal | A61F 2/28 424/424 |
| 6,454,803 B1 | 9/2002 | Romo, III | |
| 8,071,007 B1 | 12/2011 | Teoh et al. | |
| 8,480,737 B2 | 7/2013 | Hristov et al. | |
| 9,180,029 B2 | 11/2015 | Hollister et al. | |
| 9,510,940 B2 | 12/2016 | Chen et al. | |
| 9,949,823 B2 | 4/2018 | Hristov et al. | |
| 10,149,753 B2 | 12/2018 | Chen et al. | |
| 10,213,296 B2 | 2/2019 | Shim | |
| 11,071,623 B2 | 7/2021 | Rosenthal et al. | |
| 2005/0113918 A1 * | 5/2005 | Messerli | A61F 2/28 623/17.11 |
| 2010/0023130 A1 | 1/2010 | Henry et al. | |
| 2010/0168856 A1 * | 7/2010 | Long | A61F 2/30756 623/14.12 |
| 2010/0204793 A1 * | 8/2010 | Byrd | A61F 5/0102 623/10 |
| 2010/0292641 A1 * | 11/2010 | Wijay | A61M 25/10 604/103.02 |
| 2011/0264236 A1 | 10/2011 | Bassett et al. | |
| 2014/0364946 A1 | 12/2014 | Chen | |
| 2016/0015502 A1 | 1/2016 | Noble | |
| 2016/0200043 A1 | 7/2016 | Thian et al. | |
| 2018/0055643 A1 | 3/2018 | Castro et al. | |
| 2020/0188090 A1 | 6/2020 | Zopf et al. | |

FOREIGN PATENT DOCUMENTS

| | | |
|---|---|---|
| CN | 205264210 U | 5/2016 |
| DE | 4006145 A1 | 8/1990 |
| DE | 3943201 A1 | 7/1991 |
| KR | 102061194 B1 | 2/2020 |
| WO | 2016038083 A1 | 3/2016 |
| WO | WO-2018167292 A1 | 9/2018 |
| WO | WO-2018200816 A1 | 11/2018 |

OTHER PUBLICATIONS

International Search Report and Written Opinion for International Application No. PCT/US2018/029575 dated Aug. 17, 2018 (ISA/KR), 12 pages.

Cervantes, Thomas M. et al., "Design of composite scaffolds and three-dimensional shape analysis for tissue-engineered ear," J. R. Soc. Interface 10, Apr. 13, 2013 (Published online Jun. 10, 2013); DOI: 10.1098/rsif.2013.0413.

Hollister, Scott J. et al., "Design Control for Clinical Translation of 3D Printed Modular Scaffolds," Annals of Biomedical Engineering 43 (3) (Published online Feb. 10, 2015); DOI: 10.1007/s10439-015-1270-2.

Partee, Brock et al., "Selective Laser Sintering Process Optimization for Layered Manufacturing of CAPA® 6501 Polycaprolactone Bone Tissue Engineering Scaffolds," J. Manuf. Sci E. 128, pp. 531-540 (May 2006); DOI: 10.1115/1.2162589.

Zopf, David et al., "Biomechanical Evaluation of Human and Porcine Auricular Cartilage," The Laryngoscope 125, pp. E262-E268 (Published Apr. 17, 2015); DOI: 10.1002/lary.25040.

Zopf, David et al., "Computer-Aided, 3-Dimensionally Printed Porous Tissue Bioscaffolds for Craniofacial Soft Tissue Reconstruction," Otolaryngology—Head and Neck Surgery (2015), vol. 152(1), pp. 57-62; DOI: 10.1177/0194599814552065.

Correa, Bryan. J.et al.,"The Forehead Flap: The Gold Standard of Nasal Soft Tissue Reconstruction," Seminars in Plastic Surgery (2013), 27 (2), pp. 96-103; DOI:10.1055/s-0033-1351231.

Immerman, Sara et al., "Cartilage Grafting in Nasal Reconstruction," Facial Plastic Surgery Clinics of North America, vol. 19, Issue 1, (2011) pp. 175-182; DOI: 10.1016/j.fsc.2010.10.006.

Zopf et al (David A. Zopf, Anna G. Mitsak, Colleen L. Flanagan, Matthew Wheeler, Glenn E. Green and Scott J. Hollister "Computer Aided-Designed, 3-Dimensionally Printed Porous Tissue Bioscaffolds for Craniofacial Soft Tissue Reconstruction": Otolaryngology—Head and Neck Surgery, Oct. 3, 2014) (Year: 2014).

\* cited by examiner

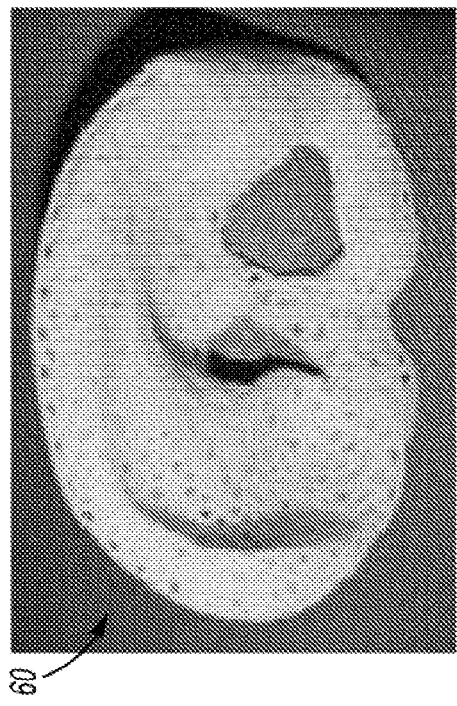
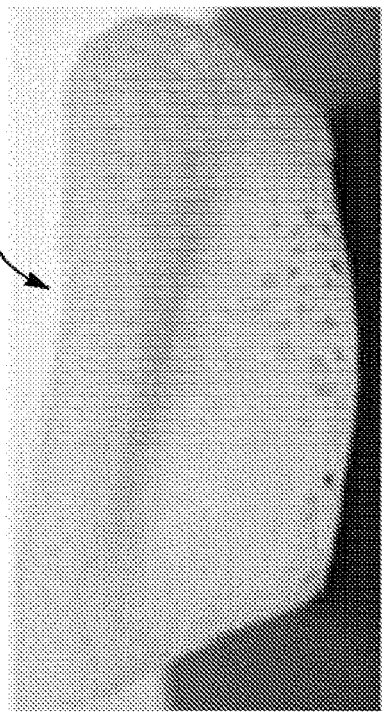
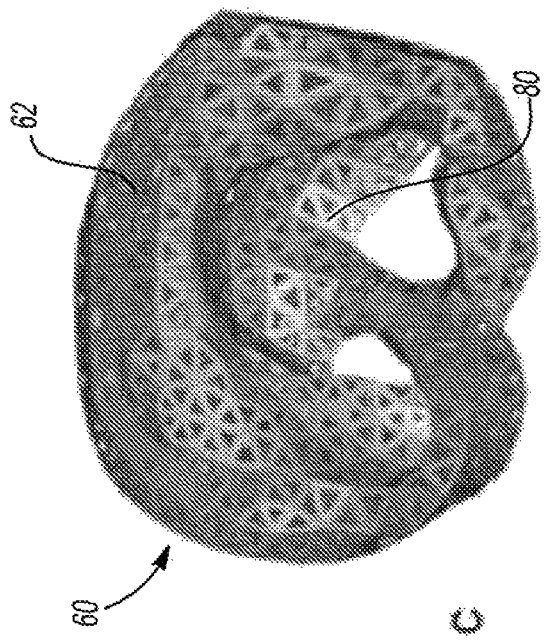
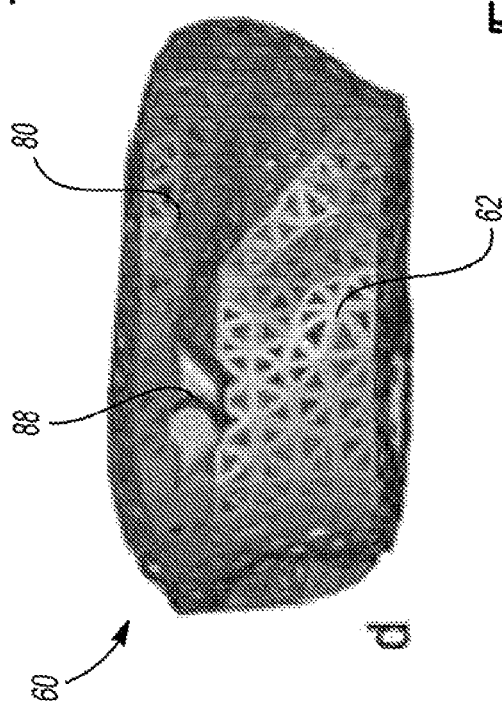
Fig-4C
Fig-4D

EAR TISSUE SCAFFOLD IMPLANT FOR AURICULAR TISSUE RECONSTRUCTION

CROSS-REFERENCE TO RELATED APPLICATIONS

This application is the U.S. National Phase Application under 35 U.S.C. 371 of International Application No. PCT/US2018/029575, filed on Apr. 26, 2018, which claims the benefit of U.S. Provisional Application No. 62/490,312, filed on Apr. 26, 2017. The entire disclosures of the above applications are incorporated herein by reference.

FIELD

The present disclosure relates to ear implant devices that serve as tissue scaffolds for tissue reconstruction and growth and methods for making and using the same.

BACKGROUND

This section provides background information related to the present disclosure which is not necessarily prior art.

Ear malformations are among the most difficult to reconstruct due to their complex geometry. Where an unsalvageable auricle arises due to trauma, oncologic resection, microtia, anotia, and the like, auricular tissue reconstruction poses one of the most technically challenging surgical procedures for reconstructive surgery. Children with facial deformities, including microtia and anotia, develop self-awareness at approximately 4 years of age and are targeted for developmentally harmful teasing and bullying. Many patients with congenital ear deformities suffer from visual impairment as well. The external ear is critical to provide support for prescription glasses, and thus a child may be further deprived of optimal vision. Patients with microtia frequently find that their glasses are poorly supported, rendering them useless to aid in vision. This poses the potential for deprivation of multiple senses and further isolation of the child. Failure to restore size, shape, and function to the ear can result in catastrophic psychosocial harm.

Currently available treatment options to treat ear defects include autogenous cartilage reconstruction, use of prostheses, including synthetic alloplastic prosthetics, or observation. Autogenous cartilage reconstruction involves carving an autogenous rib framework as foundational support for overlying soft tissue. In this procedure, a highly skilled surgeon carves an auricular cartilage framework for implantation. These techniques demand the highest level of surgical and artistic ability as they rely on freehand carving of autologous cartilage, much like carving a sculpture. Even in the best of hands, outcomes can be inconsistent and undesirable. This technique can further suffer from other limitations, including introducing multiple surgical sites to the patient (including a site to remove rib tissue, along with the implantation site), as well as being a highly complex surgery with only a limited number of surgeons available who can perform it.

The current commercially available synthetic implants may be formed of a rigid synthetic polymeric material, such as high density porous polyethylene, like the MEDPOR™ ear implant commercially available from Stryker Corp. Benefits of using a commercially available synthetic implant include avoiding donor site morbidity from rib harvesting and lower variability with the framework appearance, in that the technically demanding hand carving is not required for the framework. However, commercially available implants do not have customizable framework for patient-specific anatomy. Only a single available ear implant device is available to meet the needs of the wide range of pediatric and adult patients needing reconstruction. Furthermore, rates of fracture, exposure, extrusion, and infection of porous polyethylene are believed to be unacceptably high. Implants formed from rigid, synthetic material, like high density polyethylene in conventional prosthesis device designs, have a greater incidence of framework extrusion, dehiscence, and soft tissue necrosis than autogenous cartilage reconstruction. These complications frequently require subsequent operations and anesthetic exposures with associated risks to address these complications. Finally, synthetic implants, like the MEDPOR™ implant device, do not have the capacity for growth, nor do they serve as a platform for cell seeding or tissue ingrowth.

It would be desirable to provide an ear implant that serves as a tissue scaffold that can be used on a variety of patients, ranging from the very young to older adult patients, allowing for increased projection and scaffold expansion, along with the structural stability and ability to withstand contraction and distortion and experiencing fewer complications after implantation. It would also be desirable to provide procedures that use low cost, common surgical tools that can be employed by most surgeons and even implemented in a medical mission setting.

SUMMARY

This section provides a general summary of the disclosure, and is not a comprehensive disclosure of its full scope or all of its features.

In various aspects, the present disclosure contemplates an ear implant for auricular tissue reconstruction in a patient. In certain aspects, an implant assembly for reconstruction of auricular tissue in a patient is provided that comprises a first tissue scaffold component and a second tissue scaffold component. The first tissue scaffold component comprises a first biocompatible polymeric material having a plurality of open pores configured to support cell growth. The first tissue scaffold component defines a central void region and at least a portion of an outer ear framework of the patient after implantation. The second tissue scaffold component comprises a second biocompatible polymeric material having a plurality of open pores configured to support cell growth. The second tissue scaffold component defines a base portion after implantation into the patient. The second tissue scaffold component seats within the central void region of the first tissue scaffold component, so that the second tissue scaffold component is secured to the first tissue scaffold component.

In other aspects, the present disclosure contemplates a method for reconstructing auricular tissue in a patient. The method comprises implanting a first tissue scaffold component in an ear region of the patient. The first tissue scaffold component comprises a first biocompatible polymeric material having a plurality of open pores that support cell growth after the implanting. The first tissue scaffold component defines a central void region configured to receive a second tissue scaffold component and at least a portion of an outer ear framework of the patient. The second tissue scaffold component seats within the central void region of the first tissue scaffold component and defines a base portion of an implant assembly comprising the first tissue scaffold component and the second tissue scaffold component.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 1A-1F show an image-based design approach using medical images or other data specific to a patient to customize the size of an ear implant device prepared in accordance with certain aspects of the present disclosure.

FIGS. 2A-2B show computer-Aided Design and Three-Dimensional Printing Process for Production of Porous Bioresorbable Tissue Engineering Scaffolds. FIG. 2A show a rendering of a stereolithography (.STL) file for a cylindrical tissue engineering scaffold with 2.7 mm spherical pore internal microarchitecture. FIG. 2B shows a tissue engineering scaffold manufactured via selective laser sintering three-dimensional printing technique after cell seeding in a hyaluronic acid/collagen hydrogel and implantation into four randomized quadrants in a subcutaneous pocket on the dorsum of an athymic rat.

FIG. 3 shows a multicomponent assembly ear implant tissue scaffold device prepared in accordance with certain aspects of the present disclosure compared to a conventional commercially available high density polyethylene ear implant device.

FIGS. 4A-4D show a multicomponent assembly ear implant tissue scaffold device prepared in accordance with certain aspects of the present disclosure, where the figures on the left side show the computer-assisted-design models and the pictures on the right side show the laser-sintered polymer scaffold structure formed based on the models. FIG. 4A shows a top view of the first tissue scaffold component. FIG. 4B shows a perspective view of the second tissue scaffold component. FIG. 4C shows a top view an assembly of the first tissue scaffold component secured to the second tissue scaffold component. FIG. 4D shows a side view the assembly of the first tissue scaffold component secured to the second tissue scaffold component.

FIGS. 5A-5C show another multicomponent assembly ear implant tissue scaffold device prepared in accordance with certain other aspects of the present disclosure. FIG. 5A shows a first tissue scaffold component having an expandable opening. FIG. 5B shows the multicomponent assembly ear implant tissue scaffold device including a second tissue scaffold component seated with a central void region of the first tissue scaffold component to facilitate outward expansion of the first tissue scaffold component after implantation. FIG. 5C shows a direction of expansion of the first tissue scaffold component near the expandable opening.

Figure 8A:
Figure 8B:
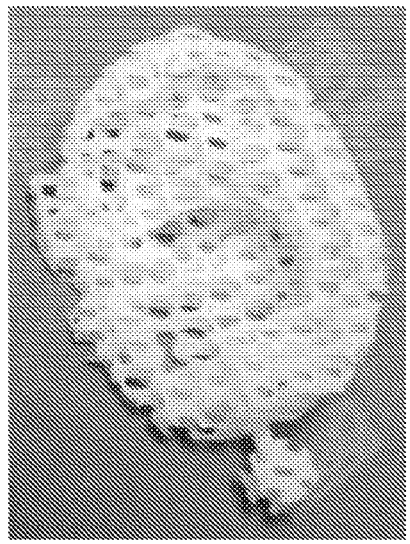
Figure 8C:
Figure 8D:
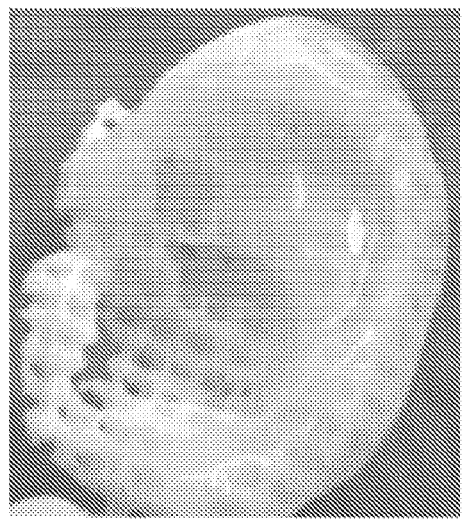

FIGS. 8A-8D are photographs showing auricular constructs with two micropore architectures, random and spherical. FIG. 8A shows a randomly distributed pore architecture in an ear implant tissue scaffold device prepared in accordance with certain aspects of the present disclosure. FIG. 8B shows a regularly distributed pattern of spherical pores in an ear implant tissue scaffold device prepared in accordance with certain aspects of the present disclosure. FIG. 8C shows an ear implant tissue scaffold device placed in a custom-designed mold that prevents leakage of a cell-collagen solution prior to gelation. FIG. 8D shows the ear implant tissue scaffold device after gelation of the cell-collagen solution on the surface.

Figure 9A:
Figure 9B:
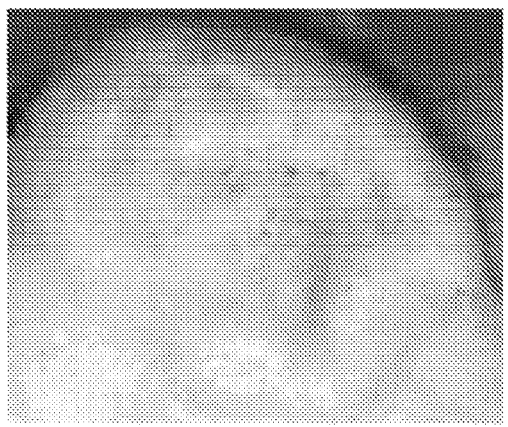
Figure 9C:
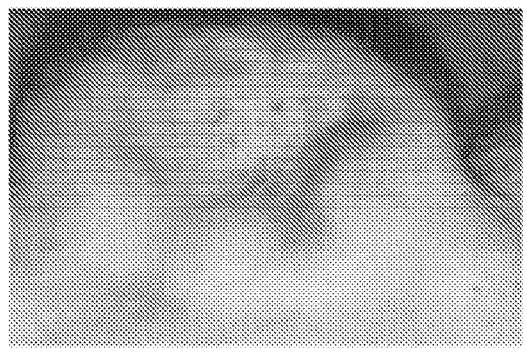

FIGS. 9A-9C show photographs of subcutaneous implantation of ear implant tissue scaffold devices that result in excellent external appearance of both anterior and posterior auricular surfaces. FIGS. 9A-9B show tissue scaffold landmarks of the ear structure, including helix, antihelix, conchal bowl, tragus, antitragus, and intertragal incisor are readily evident after subcutaneous implantation. FIG. 9C shows projection is approximately 25-30° off horizontal plane of the animal dorsum.

Figure 10A:
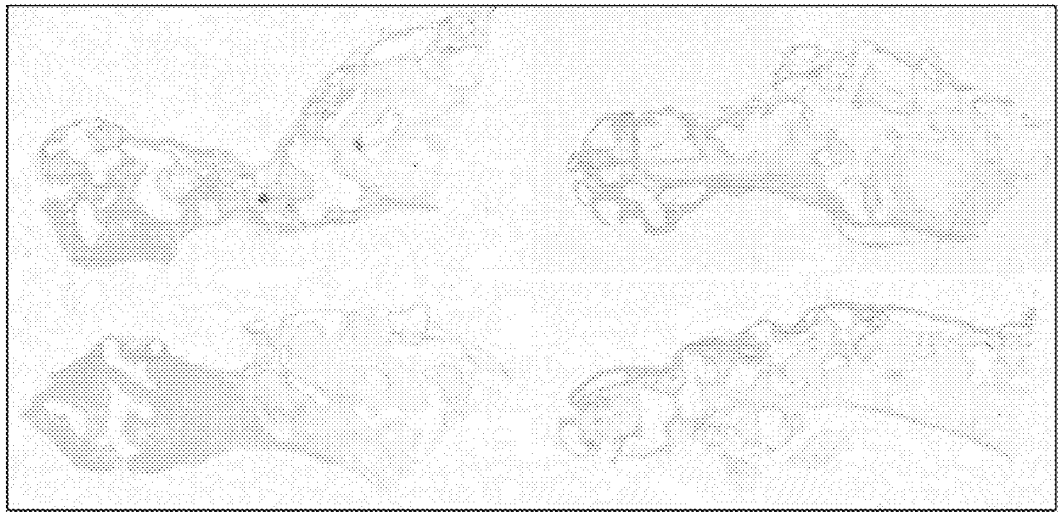
Figure 10B:
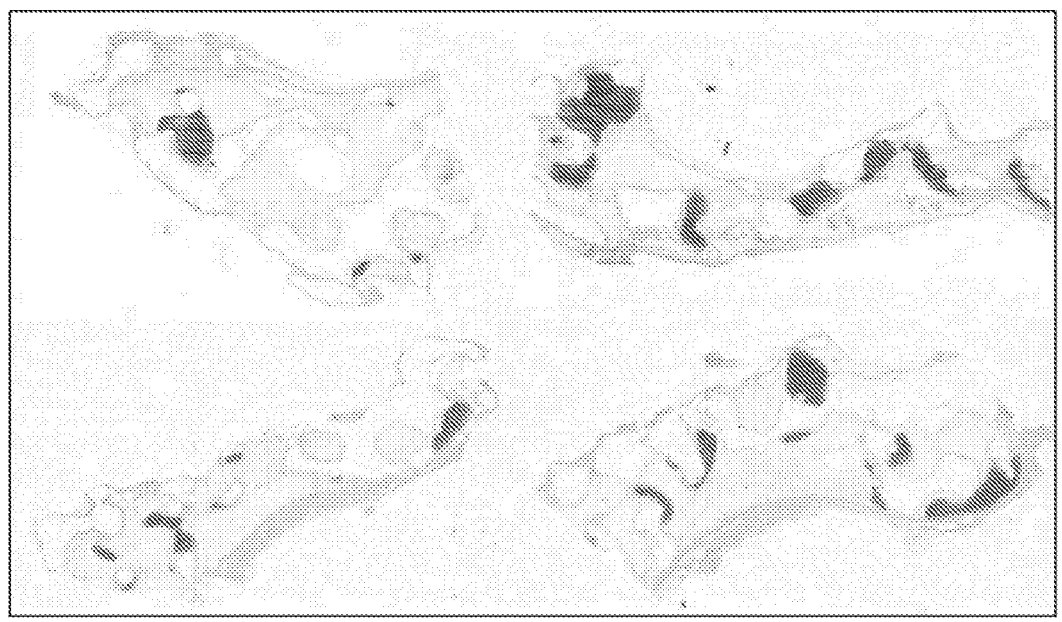

FIGS. 10A-10B show histologic analysis displays of Safranin O staining to show cellular growth for the spherical pore scaffolds in comparison to random pore scaffolds. FIG. 10A shows Safranin O staining for an ear implant tissue scaffold device having random pore architecture scaffold. FIG. 10B shows Safranin O staining for an ear implant tissue scaffold device having a spherical pore structure.

Figure 11:
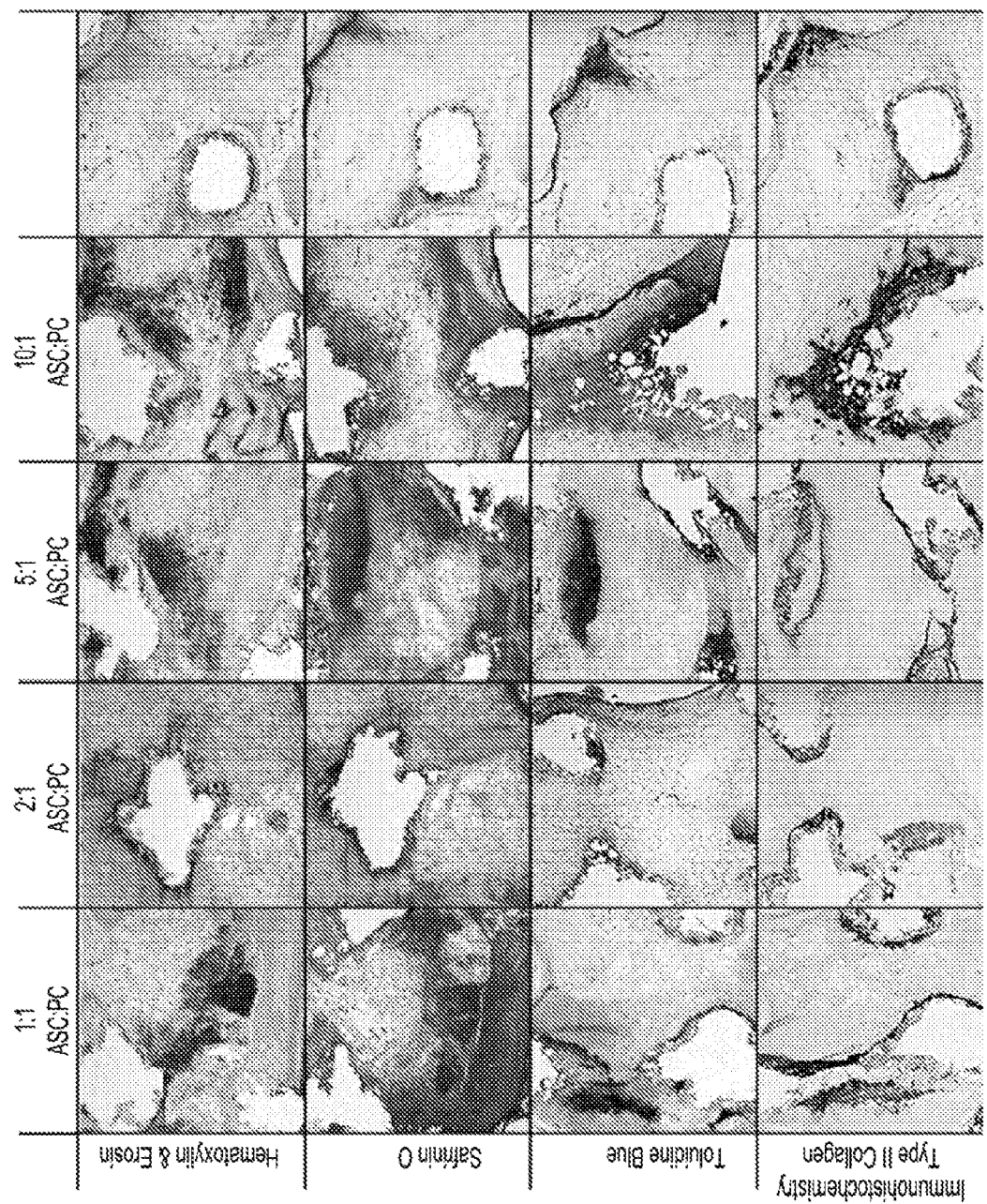

FIG. 11 shows histologic and immunohistochemical results of co-culture experimental groups at differing ratios of adipose-derived stem cells-to-chondrocytes after 4 weeks of in vitro followed by 4 weeks of in vivo culture. ASC=Adipose-derived stem cells. PC=Primary chondrocytes.

Figure 12:
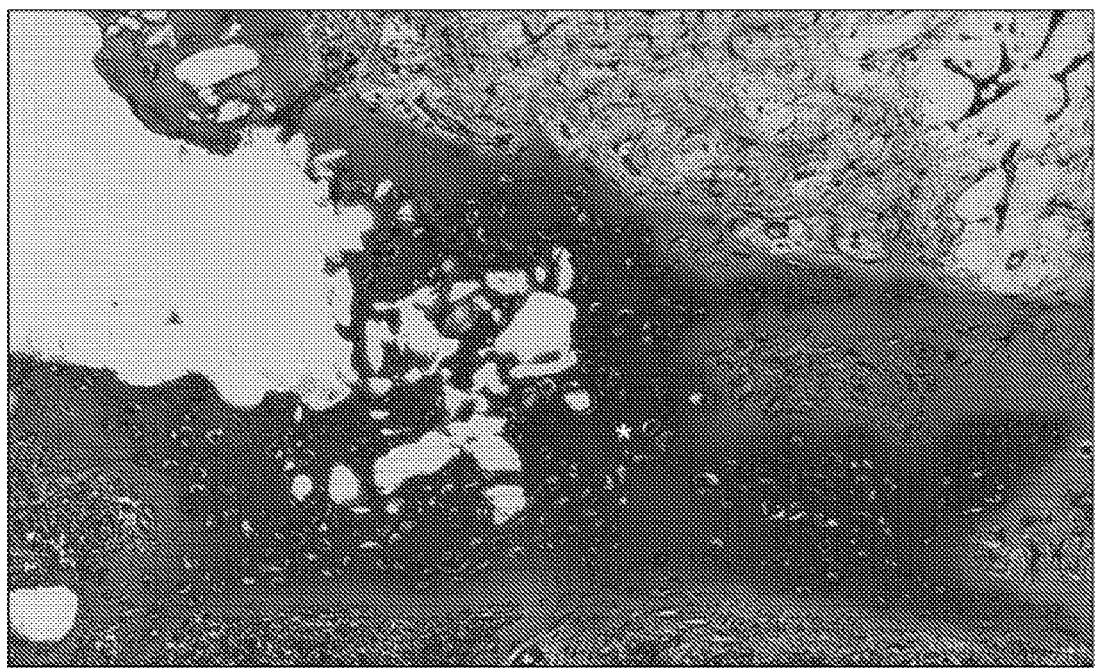

FIG. 12 shows a ten times magnification of Safrinin O staining of 5:1 ADSC-to-chondrocyte experimental groups after 4 weeks of in vivo growth. A white asterisk denotes well defined lacuna around chondrocytes within cartilage matrix.

Figure 13A:
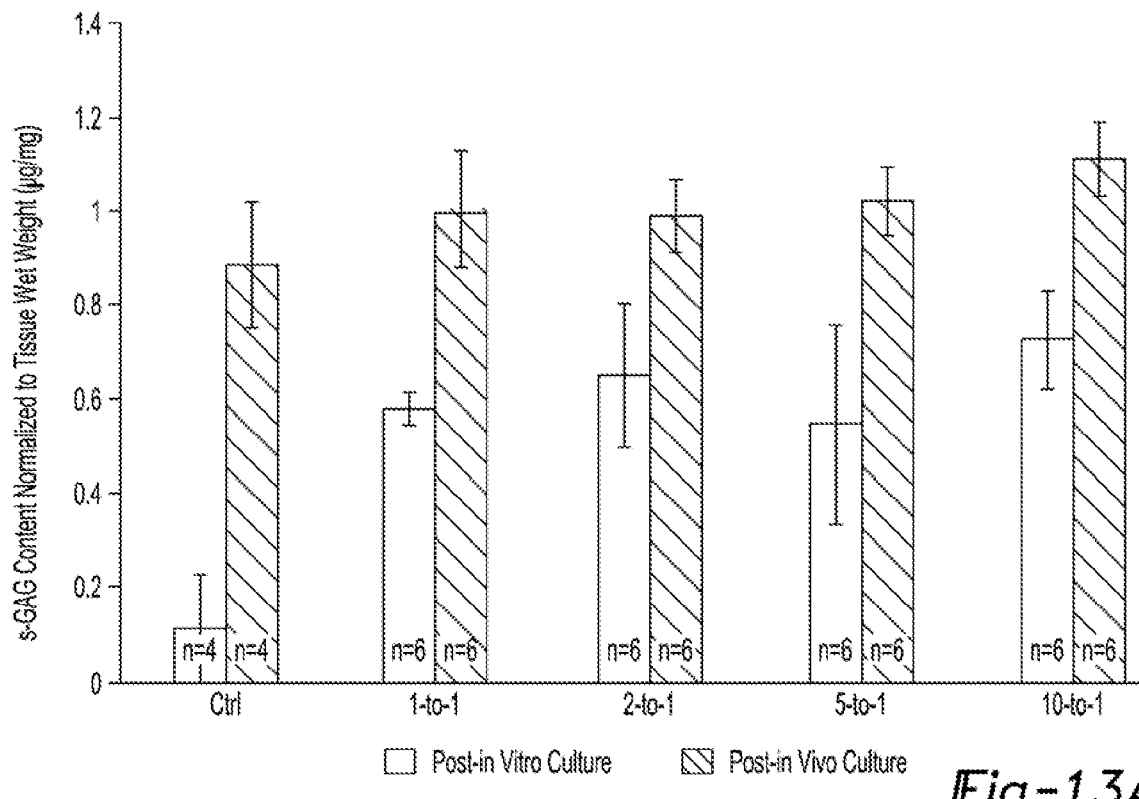
Figure 13B:
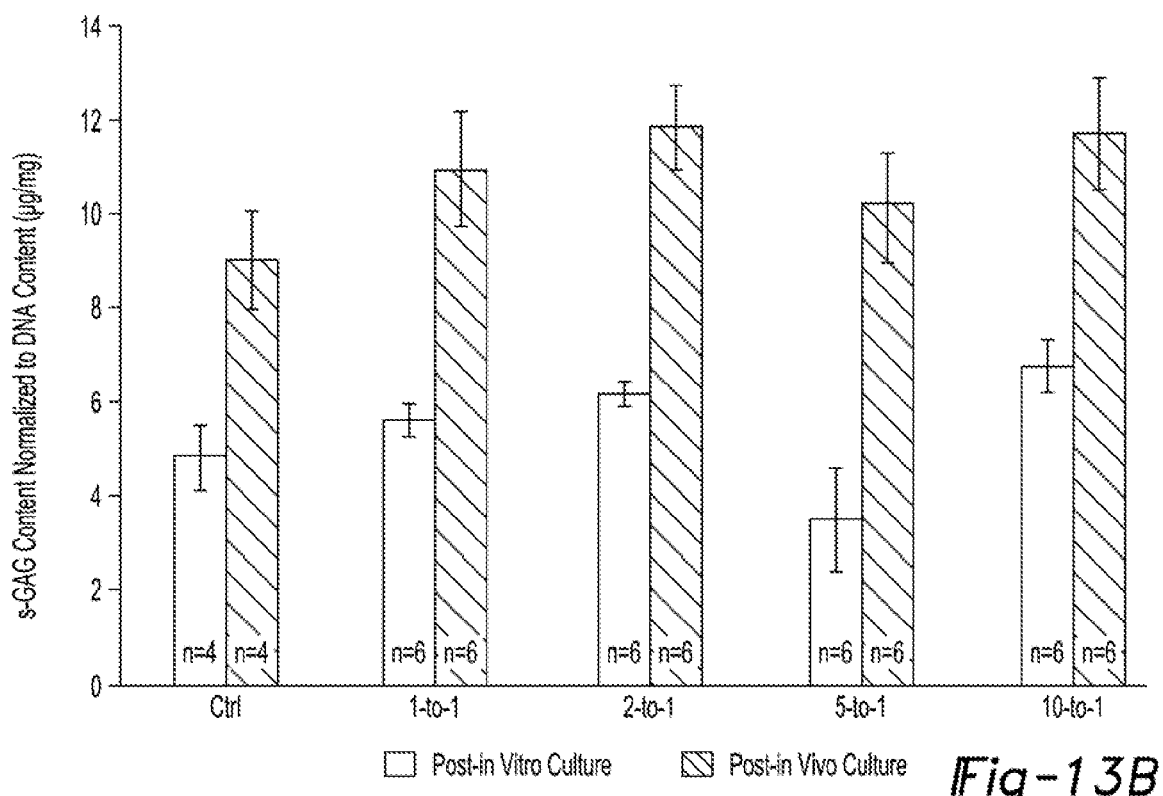

FIGS. 13A-13B show biochemical characterization for all experimental groups. All values expressed as mean values. All ratios expressed as adipose-derived stem cells-to-chrondrocytes. FIG. 13A shows s-GAG content normalized to tissue wet weight (μg/mg). FIG. 13B shows s-GAG content normalized to DNA content (μg/mg). Error bars represent standard error of the mean. s-GAG=sulfated glycosaminoglycan. DNA=dioxyribonuclease.

Figure 14:
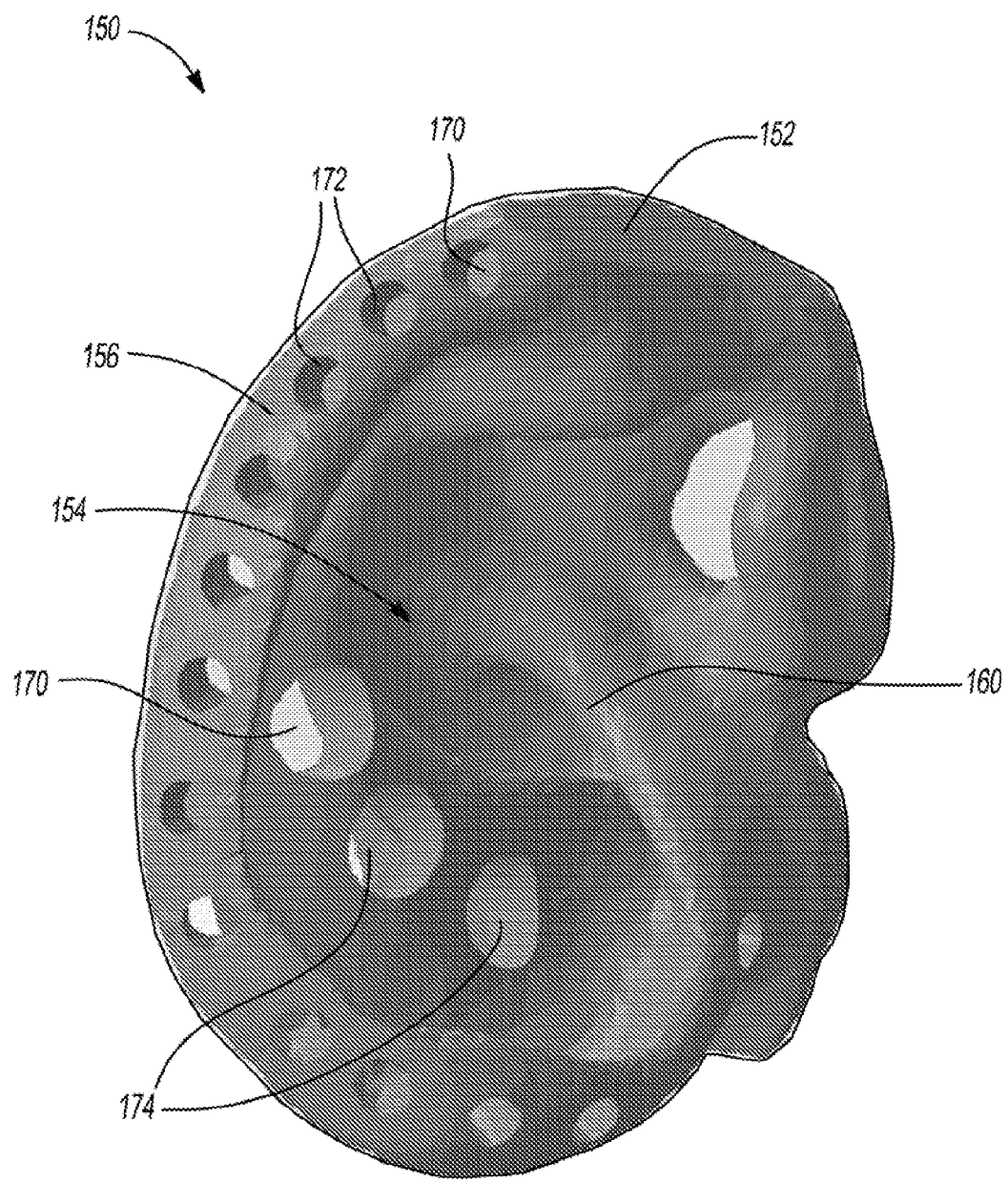

FIG. 14 shows a perspective top view of a multicomponent assembly ear implant tissue scaffold device prepared in accordance with certain aspects of the present disclosure having a plurality of hollow void regions for receiving tissue samples therein.

Corresponding reference numerals indicate corresponding parts throughout the several views of the drawings.

DETAILED DESCRIPTION

Example embodiments are provided so that this disclosure will be thorough, and will fully convey the scope to those who are skilled in the art. Numerous specific details are set forth such as examples of specific compositions, components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, elements, compositions, steps, integers, operations, and/or components, but do not preclude the presence or addition of one or more other features, integers, steps, operations, elements, components, and/or groups thereof. Although the open-ended term "comprising," is to be understood as a non-restrictive term used to describe and claim various embodiments set forth herein, in certain aspects, the term may alternatively be understood to instead be a more limiting and restrictive term, such as "consisting of" or "consisting essentially of." Thus, for any given embodiment reciting compositions, materials, components, elements, features, integers, operations, and/or process steps, the present disclosure also specifically includes embodiments consisting of, or consisting essentially of, such recited compositions, materials, components, elements, features, integers, operations, and/or process steps. In the case of "consisting of," the alternative embodiment excludes any additional compositions, materials, components, elements, features, integers, operations, and/or process steps, while in the case of "consisting essentially of," any additional compositions, materials, components, elements, features, integers, operations, and/or process steps that materially affect the basic and novel characteristics are excluded from such an embodiment, but any compositions, materials, components, elements, features, integers, operations, and/or process steps that do not materially affect the basic and novel characteristics can be included in the embodiment.

Any method steps, processes, and operations described herein are not to be construed as necessarily requiring their performance in the particular order discussed or illustrated, unless specifically identified as an order of performance. It is also to be understood that additional or alternative steps may be employed, unless otherwise indicated.

When a component, element, or layer is referred to as being "on," "engaged to," "connected to," or "coupled to" another element or layer, it may be directly on, engaged, connected or coupled to the other component, element, or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various steps, elements, components, regions, layers and/or sections, these steps, elements, components, regions, layers and/or sections should not be limited by these terms, unless otherwise indicated. These terms may be only used to distinguish one step, element, component, region, layer or section from another step, element, component, region, layer or section. Terms such as "first," "second," and other numerical terms when used herein do not imply a sequence or order unless clearly indicated by the context. Thus, a first step, element, component, region, layer or section discussed below could be termed a second step, element, component, region, layer or section without departing from the teachings of the example embodiments.

Spatially or temporally relative terms, such as "before," "after," "inner," "outer," "beneath," "below," "lower," "above," "upper," and the like, may be used herein for ease of description to describe one element or feature's relationship to another element(s) or feature(s) as illustrated in the figures. Spatially or temporally relative terms may be intended to encompass different orientations of the device or system in use or operation in addition to the orientation depicted in the figures.

Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. For example, "about" may comprise a variation of less than or equal to 5%, optionally less than or equal to 4%, optionally less than or equal to 3%, optionally less than or equal to 2%, optionally less than or equal to 1%, optionally less than or equal to 0.5%, and in certain aspects, optionally less than or equal to 0.1%.

In addition, disclosure of ranges includes disclosure of all values and further divided ranges within the entire range, including endpoints and sub-ranges given for the ranges.

As used herein, the terms "composition" and "material" are used interchangeably to refer broadly to a substance containing at least the preferred chemical constituents, elements, or compounds, but which may also comprise additional elements, compounds, or substances, including trace amounts of impurities, unless otherwise indicated.

It should be noted that the figures set forth herein are intended to exemplify the general characteristics of methods, devices, and materials, among those of the present disclosure, for the purpose of the description of certain embodiments. These figures may not precisely reflect the characteristics of any given embodiment, and are not necessarily intended to fully define or limit specific embodiments within the scope of this disclosure.

Example embodiments will now be described more fully with reference to the accompanying drawings.

In various aspects, the present disclosure provides ear implant devices for reconstructing tissue in a patient. The patient may be an animal, such as a mammal, including a human. The reconstructed tissue may be auricular tissue, including cartilage. In certain variations, the ear implant device is a multi-component implant assembly that comprises a first component and a second distinct component that can be implanted via surgery into or on the patient. In various aspects, the first component and the second component are tissue scaffolds that promote cell ingrowth. Thus, a first tissue scaffold component comprises a plurality of open pores configured to support cell growth and likewise, a second tissue scaffold component comprises a plurality of open pores configured to support cell growth. In various aspects, the first tissue scaffold component comprises a first biocompatible polymeric material and the second tissue scaffold component comprises a second biocompatible polymeric material. Specific materials to be used in the implant devices of the present technology that are biocompatible are preferably biomedically acceptable. Such a "biomedically acceptable" material is one that is suitable for use with humans and/or animals without undue adverse side effects (such as toxicity, irritation, and allergic response) commensurate with a reasonable benefit/risk ratio. The first biocompatible polymeric material and the second biocompatible polymeric material may be the same or distinct compositions. In certain variations, the first biocompatible polymeric material and/or the second biocompatible polymeric material may be composite materials having a reinforcement phase or material distributed therein.

In certain embodiments, the ear implant devices of the present technology comprise a biocompatible polymer, such as a biodegradable polymer. The first biocompatible polymeric material and the second biocompatible polymeric material may independently comprise a biocompatible or biomedically acceptable polymer. The biocompatible polymer may be biodegradable or non-biodegradable. The term "biodegradable" as used herein means that the implant comprising the polymer is slowly dissolved or disintegrated under physiological conditions in the human or other animal subject for a certain time and at some point only its degradation products are present in the body in a dissolved or comminuted form. At this point, solid components or fragments of the implant either do not exist anymore or are so small as to be non-harmful or transported away by the subject's circulatory system. The degradation products are desirably substantially harmless in physiological terms and lead to molecules that either occur naturally in the human or other animal subject or can be excreted by the human or other animal subject.

Biodegradable polymers include polycaprolactone, polysebacic acid, poly(octaindiolcitrate), polydioxanone, polygluconate, poly(lactic acid) polyethylene oxide copolymer, modified cellulose, polyhydroxybutyrate, polyamino acids, polyphosphate ester, polyvalerolactone, poly-6-decalactone, polylactonic acid, polyglycolic acid, polylactides, polyglycolides, copolymers of the polylactides and polyglycolides, polye-caprolactone, polyhydroxybutyric acid, polyhydroxybutyrates, polyhydroxyvalerates, polyhydroxybutyrate-co-valerate, poly(1,4-dioxane-2,3one), poly(1,3-dioxane-2-one), poly-para-dioxanone, polyanhydrides, polymaleic acid anhydrides, polyhydroxy methacrylates, fibrin, polycyanoacrylate, polycaprolactone dimethylacrylates, poly-3-maleic acid, polycaprolactone butyl acrylates, multiblock polymers from oligocaprolactonediols and oligodioxanonediols, polyether ester multiblock polymers from PEG and poly (butylene terephthalates), polypivotolactones, polyglycolic acid trimethyl carbonates, polycaprolactone glycolides, poly (methyl glutamate), poly (DTH-iminocarbonate), poly (DTE-co-DT-carbonate), poly(bisphenol A-iminocarbonate), polyorthoesters, polyglycolic acid trimethyl carbonate, polytrimethyl carbonates, polyiminocarbonates, poly(N-vinyl)-pyrrolidone, polyvinyl alcohols, polyester amides, glycolized polyesters, polyphosphoesters, polyphosphazenes, poly[p-(carboxyphenoxy) propane], polyhydroxy pentanoic acid, polyanhydrides, polyethylene oxide propylene oxide, and combinations thereof. In various embodiments, a preferred biodegradable biocompatible polymer that forms the ear implant device comprises, or consists essentially of, polycaprolactone.

In various embodiments, the ear implant device comprising the biodegradable biocompatible polymer allows the auricular tissue to grow over and into the tissue scaffold and heal naturally. The implant may then biodegrade or resorb in the subject or patient. Having the implant biodegrade will not inhibit regrowth in adults or growth in children. In various embodiments, the ear implant device is designed to have a degradation time that coincides with the healing time that permits regrowth of the defect in the patient. "Degradation time" refers to the time for the ear implant device implanted to substantially and fully dissolve, disintegrate, or resorb. Depending upon the patient and the time needed for recuperation and regeneration of the auricular tissue, the degradation time may be about 3 weeks to about 60 months (5 years), or about 2 months to about 40 months (3.33 years), or about 6 months to about 36 months (3 years), or about 12 months to about 24 months (2 years). As noted above, in certain embodiments, a preferred biodegradable biocompatible polymer used to form the ear implant device comprises polycaprolactone, which desirably enables a degradation time of 6 months to about 36 months (3 years) under normal physiological conditions when implanted in an animal subject/patient.

The term "non-biodegradable polymer" as used herein means that the biocompatible or biomedically acceptable polymer forming the implant will not dissolve in the human or animal subject. These polymers do not substantially resorb, dissolve or otherwise degrade after implantation in a human or animal subject, under typical physiological conditions.

In certain embodiments, the ear implant device of the present disclosure optionally comprises a non-biodegradable biocompatible polymer. Suitable biomedically acceptable non-biodegradable biocompatible polymers include polyaryl ether ketone (PAEK) polymers (such as polyetherketoneketone (PEKK), polyetheretherketone (PEEK), and polyetherketoneetherketoneketone (PEKEKK)), polyolefins (such as ultra-high molecular weight polyethylene, which may be crosslinked, and fluorinated polyolefins such as polytetrafluorethylene (PTFE) or high density porous polyethylene), polyesters, polyimides, polyamides, polyacrylates (such as polymethylmethacrylate (PMMA)), polyketones, polyetherimide, polysulfone, polyurethanes, and polyphenolsulfones. The ear implant device may comprise multiple biocompatible polymers, including one or more biodegradable biocompatible polymers, one or more non-biodegradable biocompatible polymers, and any combinations thereof.

The ear implant device of the present technology can further comprise one or more bioactive materials. More specifically, the first biocompatible polymeric material and the second biocompatible polymeric material may independently comprise a bioactive material. Depending on such factors as the bioactive material, the structure of the ear implant device, and the intended use of the implantable ear reconstruction device, the bioactive material may be coated on a surface of the first tissue scaffold component or the second tissue scaffold component, coated or otherwise infused in the pores or openings of the first tissue scaffold component or the second tissue scaffold component, or mixed or compounded within the first biocompatible polymeric material and the second biocompatible polymeric material of the ear implant device.

Bioactive materials can include any natural, recombinant or synthetic compound or composition that provides a local or systemic therapeutic benefit. In various embodiments, the bioactive material promotes healing and growth of an ear tissue resulting from a defect, including anotia, microtia, injuries or wounds resulting from trauma or surgery (such as oncologic surgical intervention). Bioactive materials among those useful herein include cell adhesion factors, isolated tissue materials, growth factors, peptides and other cytokines and hormones, pharmaceutical actives, nanoparticles, and combinations thereof. Cell adhesion factors include, for example, the RGD (Arg-Gly-Asp) sequence or the IKVAV (Ile-Lys-Val-Ala-Val) sequence. Growth factors and cytokines useful herein include transforming growth factor-beta (TGF-$\beta$), including the five different subtypes (TGF-$\beta$ 1-5); bone morphogenetic factors (BMPs, such as BMP-2, BMP-2a, BMP-4, BMP-5, BMP-6, BMP-7 and BMP-8); platelet-derived growth factors (PDGFs); insulin-like growth factors (e.g., IGF I and II); fibroblast growth factors (FGFs), vascular endothelial growth factor (VEGF), epidermal growth factor (EGF) and combinations thereof. Examples of pharmaceutical actives include antimicrobials, antifungals, chemotherapeutic agents, and anti-inflammatories. Examples of antimicrobials include triclosan, sulfonamides, furans, macrolides, quinolones, tetracyclines, vancomycin, cephalosporins, rifampins, aminoglycosides (such as tobramycin and gentamicin), and mixtures thereof.

In certain variations, an ear implant device comprises a bioactive material in the form of a biomaterial that may be selected from the group consisting of: an isolated tissue material, a hydrogel, acellularized dermis, an acellularized tissue matrix, a composite of acellularized dermis matrix and designed polymer, or a composite of acellularized tissue matrix and designed polymer, and combinations thereof. An isolated tissue material may include an autologous or allogeneic tissue sample (such as an explant harvested in the patient by a punch biopsy to provide tissue sample). In other aspects, an isolated tissue material may include isolated or cultured cells (such as chondrocyte cells, hemopoietic stem cells, mesenchymal stem cells, such as adipose-derived mesenchymal stem cells, endothelial progenitor cells, fibroblasts, reticulacytes, and endothelial cells), whole blood and blood fractions (such as red blood cells, white blood cells, platelet-rich plasma, and platelet-poor plasma), collagen, fibrin, acellularized dermis, and the like. In one embodiment, the isolated tissue biomaterial may comprise a combination of porcine adipose-derived stem cells and/or bone marrow derived or induced pluoripotent stem cells with chondrocytes, which may be combined at ratios of about 1:1 to 10:1. Hydrogels are materials formed from lightly-cross-linked networks of natural or synthetic polymers, such as saccharides, which have high water contents such as 90% weight per volume or greater. Hydrogel crosslinking can be achieved by various methods including ionic, covalent chemical, or UV-initiated chemical crosslinking. Hydrogels used in the present disclosure are preferably biocompatible. Hydrogels may be formed from hyaluronic acid/hyaluronan, sodium alginate, polyethylene glycol (PEG), polyethylene glycol diacrylate (PEGDA), 2-hydroxyethyl methacrylate (HEMA)/poly(2-hydroxyethyl methacrylate) (pHEMA), polymethyl methacrylate (PMMA), polyacrylic acid, chitosan, poly(amino acids), poly(N-isopropylacrylamide) (PNIPAM), collagen, gelatin, fibronectin, chondroitin sulfate, surfactant gels (having greater than about 20% weight per volume poloxamers (e.g., commercially available as PLURONIC™ and BRIJ™), polydimethylsiloxane (PDMS) or dimethicone, epoxy, polyurethane, and the like. In one embodiment, a suitable hydrogel based biomaterial may comprise hyaluronic acid and Type I collagen. In certain aspects, an implantable ear device may have a biomaterial disposed on one or more surfaces that will contact tissue in the patient upon implantation of the ear implant device.

In certain variations, the first tissue scaffold component consists essentially of the first biocompatible polymeric material and an optional bioactive agent/biomaterial and the second tissue scaffold component consists essentially of the biocompatible polymeric material and an optional bioactive agent/biomaterial prior to implantation in the patient.

The present disclosure thus contemplates scaffold based tissue engineering for ear reconstruction. The ear implant assembly may be implanted in a patient selected from prefabricated implant devices having common sizes and dimensions or may be customized to a patient by using an image-based design approach to tailor the design to a specific human or animal subject. Where the ear implant device is manufactured for a specific patient, it provides a personalized, customizable solution for several possible applications in ear reconstruction, including reconstruction of microtia, anotia, or congenital deformity, reconstruction in oncologic resection, and reconstruction in trauma or blast injury, by way of example. Such techniques provide the ability to incorporate age, gender, and ethnic specific properties to these ear implant devices. The image-based design approach uses medical images or other data that is specific to the patient to customize the size of the ear implant device. Scaffold implants can be produced from extrapolation of ear defects or virtual repair of congenital malformations. Also, mirrored scaffolds allowing perfect symmetry in repair can be produced.

Figure 1C:
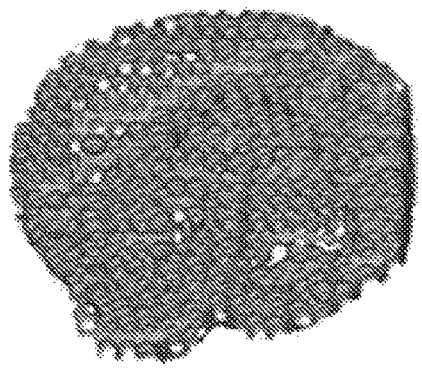
Figure 1F:
Figure 1B:
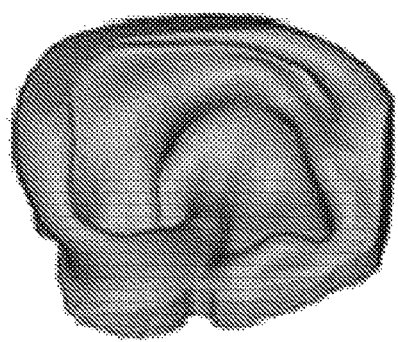
Figure 1E:
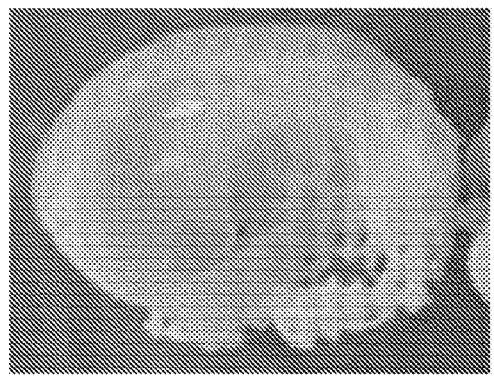
Figure 1A:
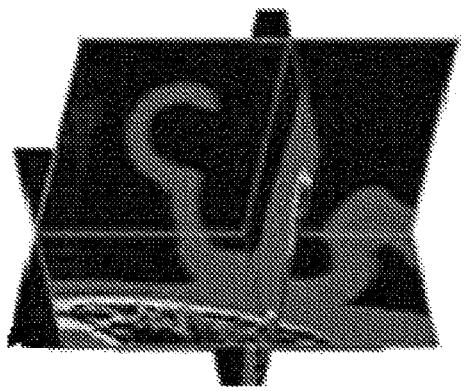

With reference to FIGS. 1A-1B, first specific medical images and/or parameters are obtained from one or more imaging systems such as computed tomography (CT), a CT-fluoroscopy, fluoroscopy, magnetic resonance imaging (MRI), ultrasound, positron emission tomography (PET) and X-Ray systems or any other suitable imaging systems. In certain aspects, an ear implant scaffold may be produced from a laser or light 3D scan, multipod photography, or pre-existing CT/MRI scan of the patient.

The medical image data and/or parameters received from the imaging system provide a two-dimensional (2D), three-dimensional (3D) or four-dimensional (4D) model of an anatomical structure, system or region of the patient, here the ear region of the patient. The image-based design of the 2D, 3D or 4D model may be created using MATLAB®, Mathematica®, or other computer-aided-designed (CAD) software design programs known in the art. For converting the design into a usable format for rapid prototyping and computer-aided manufacturing, a STL file format may be created. This file format is supported by many software packages such as Mimics® by Materialise, MATLAB®, IDL, and Amira®. More specifically, Digital Imaging and Communications in Medicine (DICOM) data is shown for the anatomic structure of interest (e.g., an ear region) of a patient in FIG. 1A and used to generate a three-dimensional model of the structure shown in FIG. 1B.

This 2D, 3D or 4D model of the ear implant device of the present technology may then be used to manufacture the ear implant device. The implant device may be made by a variety of suitable methods, including methods comprising solid free-form fabrication (SFF) techniques, such as laser sintering, stereolithography, 3D printing, injection molding and the like. In various embodiments, the preferred method is an additive manufacturing process of laser sintering. Laser sintering is a process involving the construction of a three-dimensional article by selectively projecting a laser beam having the desired energy onto a layer of particles of the polymer material to be sintered. The laser sintering process can be paired with medical image data and/or parameters received from the imaging system for producing a customized ear implant device of the present technology. The model in FIG. 1B is thus converted into a porous structure using negative Boolean operations shown in FIG. 1C and manufactured from polycaprolactone using an additive manufacturing process, such as selective laser sintering three-dimensional (3D) printer.

Figure 1D:
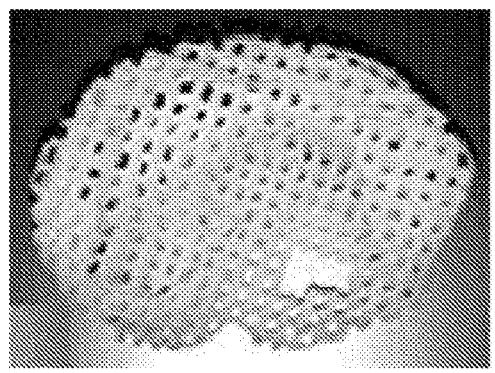

In FIG. 1D, the pores of the bioresorbable scaffold are then seeded with cells suspended in a hyaluronic acid/collagen hydrogel (shown in FIG. 1E) prior to implantation. FIG. 1F shows an ear implant after implantation and tissue growth and reconstruction. In this manner, the present disclosure contemplates forming mirrored tissue scaffolds allowing perfect symmetry in repair. Such techniques can produce patient specific anatomic soft tissue implants and tissue engineering scaffolds that can reproduce complex craniofacial structures with high fidelity.

Figure 2A:
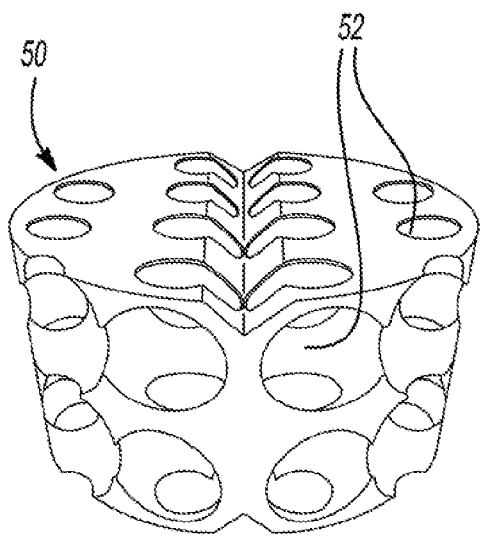
Figure 2B:
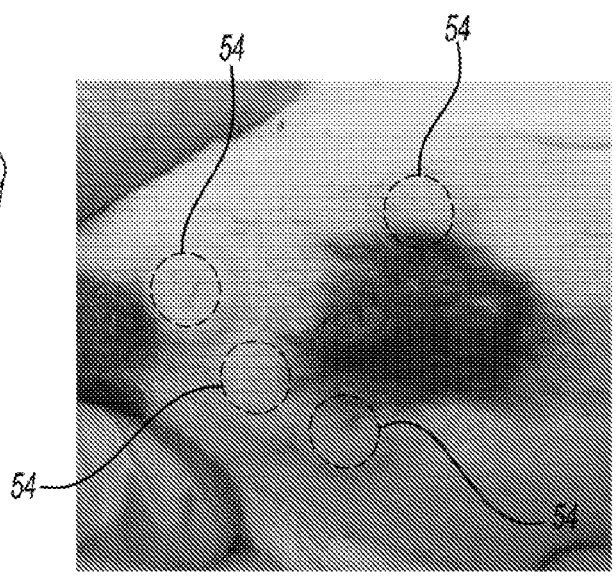

FIGS. 2A-2B show a computer-aided design (CAD) and a three-dimensional printing process for production of a porous bioresorbable tissue engineering scaffold. In FIG. 2A, a rendering of stereolithography (.STL) file for an example cylindrical tissue engineering scaffold 50 having a plurality of open and interconnected pores 52 with a 2.7 mm spherical pore internal microarchitecture prepared in accordance with certain aspects of the present disclosure is shown. This STL file can form a final tissue engineering scaffold via selective laser sintering three-dimensional printing technique of a biocompatible polymer, such as polycaprolactone. Scaffold features as small as about 70 µm can be successfully reproduced with this approach. FIG. 2B shows final tissue engineering scaffolds after cell seeding in a hyaluronic acid/collagen hydrogel implanted into four randomized quadrants in a subcutaneous pocket on the dorsum of an athymic rat.

Figure 3:
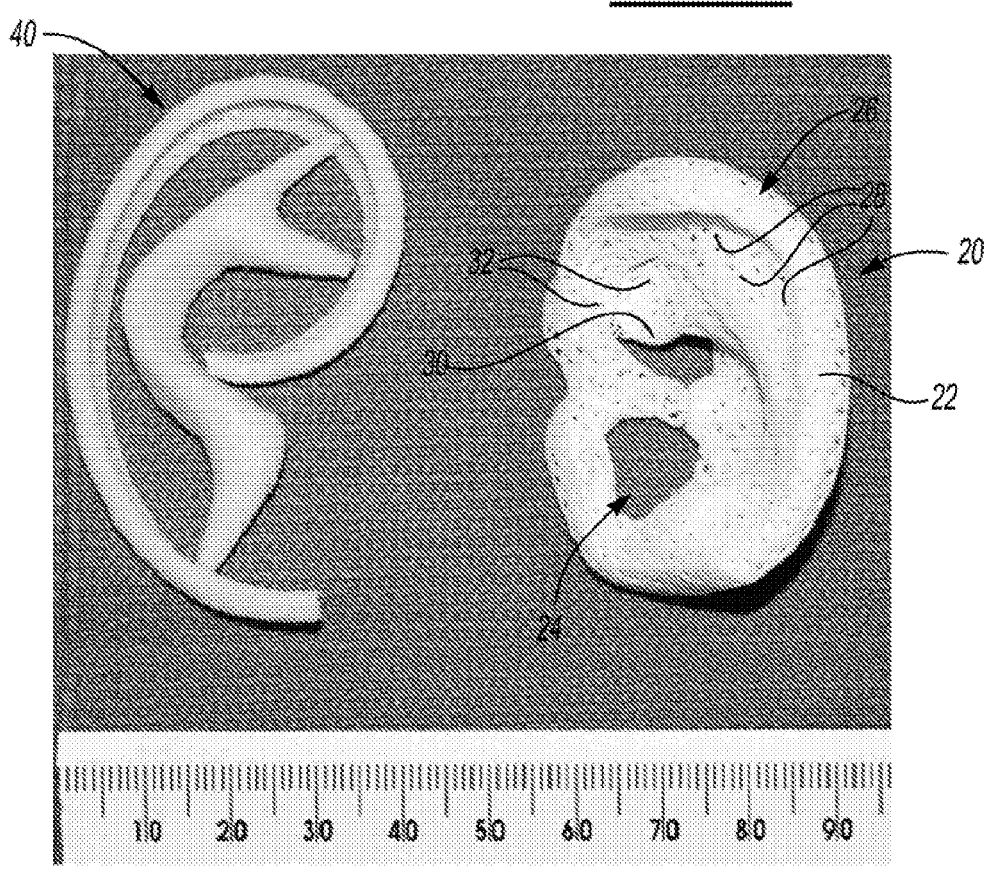

Referring to FIG. 3, an ear implant device 20 is shown that is a multicomponent assembly that serves as a tissue scaffold when implanted. The ear implant device 20 includes a first tissue scaffold component 22 that defines a central void region 24 and at least a portion of an outer ear framework 26 of the patient. By outer framework, it is meant that at least a portion of the auricle of the ear, including helix, lobule, antitragus, and/or tragus regions, may be reconstructed via tissue growth. In certain variations, the outer ear framework may be an enclosed ring structure defining the central void region 24. In other variations, the outer ear framework may have a C-shape with a narrow opening that defines the central void region 24. The first tissue scaffold component 22 comprises a first biocompatible polymeric material having a first plurality of open pores 28 configured to support cell growth. A first plurality of open pores 28 that can support cell growth may have an average pore diameter of greater than or equal to about 70 µm to less than or equal to about 8 mm. The plurality of open pores desirably is interconnected and provides fluid flow between the pores to permit flow of nutrients and fluids therebetween. The plurality of open pores may be regularly distributed in a repeating or random pattern, but in certain preferred aspects, are regularly and evenly distributed within the scaffold. The pores may have a variety of shapes, but in certain variations, may be a round shape, such as spherical. The scaffold may optionally have a porosity of greater than or equal to about 50% by volume to less than or equal to about 95% by volume voids or open pores, optionally greater than or equal to about 50% by volume to less than or equal to about 70% by volume open pores. Such pore properties can facilitate and support good cell and tissue ingrowth when the scaffold device is implanted into the patient.

The ear implant device 20 also includes a second tissue scaffold component 30 defines a base portion. After implantation into the patient, the second tissue scaffold component 30 seats within a portion of the central void region 24 of the first tissue scaffold component 22, so that the second tissue scaffold component 30 is secured to the first tissue scaffold component 22 and thus defines an ear implant scaffold assembly. The base portion may define at least a part of the triangular fossa, antihelix, and/or concha regions of the ear may be recreated and in certain variations and the base portion will recreate the central tissue structures inside the ear outer framework, although in certain embodiments, the second tissue scaffold component may also extend into a portion of the outer ear framework, for example, extending into the helix region of the ear. The second tissue scaffold component 30 comprises a second biocompatible polymeric material having a second plurality of open pores 32 configured to support cell growth. The second plurality of open pores 32 can have the same properties as the first plurality of open pores 28 discussed above. As can be seen, the ear implant has a width of approximately 30 mm and a height of approximately 72 mm, although these dimensions are merely exemplary and non-limiting.

Non-limiting examples of suitable dimensions for ear implants formed in accordance with certain aspects of the present disclosure are as follows. The ear implant device, for example, the assembled components in a multicomponent implant, may have a width ranging from greater than or equal to about 20 mm to about 50 mm and a height ranging from greater than or equal to about 35 mm to about 75 mm.

For purposes of comparison, a high density porous polyethylene MEDPOR™ ear implant 40 that is commercially available from Stryker Corp. is shown for comparison in FIG. 1. Prior to implantation, the components are fused to one another. As noted previously, MEDPOR™ ear implants are not tissue scaffolds and do not have the capacity for growth, because no cell seeding or tissue ingrowth occurs such high density porous polymeric implants. Further, only a single sized ear construct is available to meet the needs of the wide range of pediatric and adult patients needing reconstruction. The rigidity of the MEDPOR™ ear implant combined with other shortcomings in the design result in high levels of complications, fracture, exposure, extrusion, and infection of porous polyethylene device after implantation into patients.

Figure 4A:
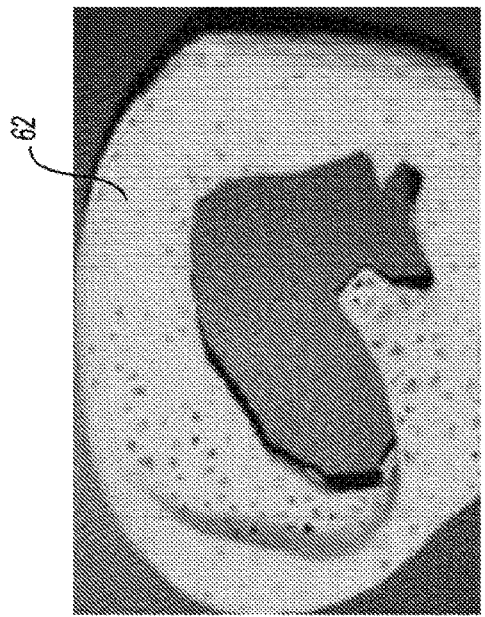
Figure 4A:
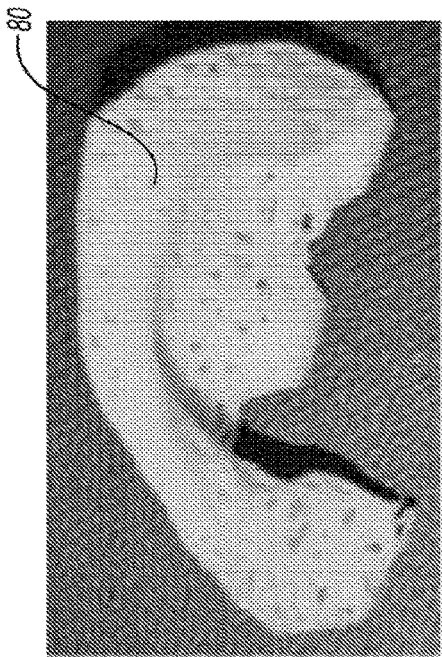

Referring to FIGS. 4A-4D, a multicomponent ear implant assembly 60 is shown that serves as a tissue scaffold when implanted in a patient (best seen in FIGS. 4C-4D). Each figure shows a computer-assisted-model of the component and the laser sintered scaffold formed from the model. As shown in FIG. 4A, the ear implant assembly 60 includes a first tissue scaffold component 62 that defines a central void region 64 and at least a portion of an outer ear framework 66 of the patient. The first tissue scaffold component 62 comprises a first biocompatible polymeric material having a first plurality of open pores 68 configured to support cell growth. The first plurality of open pores 68 have a tetrahedral unit shape and may have the dimensions and properties described previously above in the context of FIG. 3. The first tissue scaffold component 62 further comprises a first interlock member 70. As shown, the first interlock member 70 defines a rectangular shaped void 72.

Figure 4B:
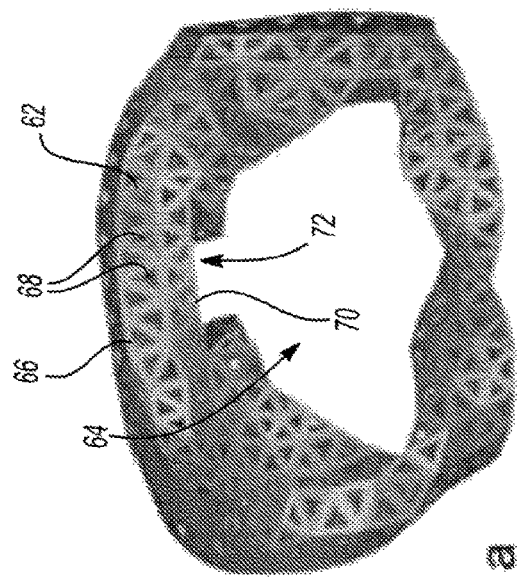
Figure 4B:
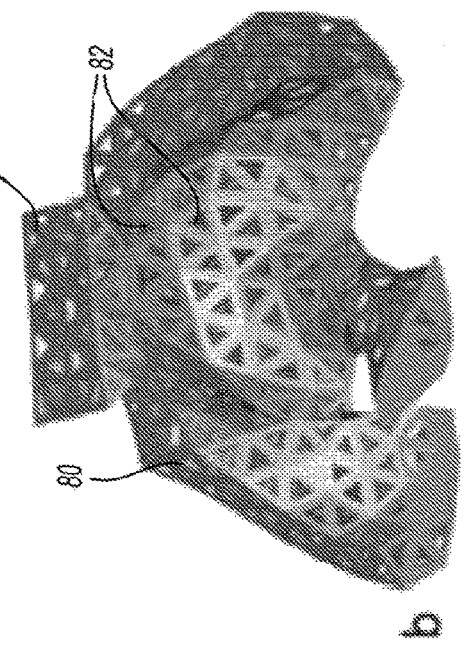

The multicomponent ear implant assembly 60 also includes a second tissue scaffold component 80 that defines a base portion of the assembly 60 as shown in FIG. 4B. After implantation into the patient, the second tissue scaffold component 80 seats within a portion of the central void region 64 of the first tissue scaffold component 62, so that the second tissue scaffold component 80 is secured to the first tissue scaffold component 62. The second tissue scaffold component 80 comprises a second biocompatible polymeric material having a second plurality of open pores 82 configured to support cell growth. The second plurality of open pores 82 can have the same properties as the first plurality of open pores 68 discussed above or in the context of FIG. 3. The second tissue scaffold component 80 further comprises a second interlock member 84. The second interlock member 84 may be in a shape of a rectangular projection. Notably, other shapes complementary with the opposing interlock member are also contemplated. The first interlock member 70 on the first tissue scaffold component 62 and the second interlock member 84 on the second tissue scaffold component 80 are coupled together and secure the first tissue scaffold component 62 to the second tissue scaffold component 80, as shown in FIGS. 4C and 4D. The first and second interlock features may together define a dove tail interlock assembly, an offset snap assembly, have contrapositive interlocking shapes, and the like to secure the components together in the assembly.

In certain aspects, a multicomponent ear implant assembly 60 like that shown in FIGS. 4A-4D may be used in a multistage implantation procedure. In certain variations, the first tissue scaffold component 62 may first be implanted in the patient to facilitate ingrowth of cells and tissue over and within the scaffold to define an outer ear framework. The outer ear framework may have a relatively low profile without significant elevation. After a sufficient amount of tissue growth has occurred, then a second surgical procedure may implant the second tissue scaffold component 80 into the patient. The first interlock member 70 and the second interlock member 84 are coupled together during this procedure to secure the first tissue scaffold component 62 to the second tissue scaffold component 80. Notably, the design of the ear implant shown in FIGS. 4A-4D and more specifically, the second interlock member 84 of the second tissue scaffold component 80 is configured to elevate the entire implant assembly 60 and serves as a "kickstand" or "prop" of the assembly.

In this manner, the introduction of the second tissue scaffold component 80 serves to raise a height and profile of the implant assembly 60, thus facilitating profiling to approximate natural ear shape in the second stage of growth within the tissue scaffold. The low profile of the first tissue scaffold component 62 reduces the incidence of dehiscence. Then, the second tissue scaffold component 80 is implanted underneath the initial conformational shape of the auricle corresponding to the first tissue scaffold component 62 and thus elevates the auricle to obtain full projection. The secondary tissue scaffold component 80 can snap into the primary implanted first tissue scaffold component 62. Such a multistage implantation procedure may be particularly advantageous where the ear size may change (for example, in a growing child) or where the tissue at the target site is too thin or delicate to accommodate the height of the entire assembly in a single implantation procedure. In alternative aspects, the components of the multicomponent ear implant assembly 60 may be secured prior to an initial implantation surgery and implanted as an entire assembly in one procedure.

In certain variations, second interlock member 84 rectangular projection may comprise a tissue expansion device that may facilitate additional tissue expansion after implantation. It should be noted that other regions of the implant assembly 60 may have a tissue expansion device and it is not limited to the rectangular projection of the second interlock member 84. For example, the tissue expander may be a bladder or balloon into which gas or fluid may be serially injected to gradually expand the expansion device and surrounding tissue. Similarly, the tissue expansion device may be an osmotic expansion device that gradually increases in volume over time to facilitate tissue expansion. As noted above, where the second interlock member 84 is a kickstand that serves as a way to increase height and profile of the implant assembly 60, such tissue expansion may increase the height of the overall implant assembly 60. In various aspects, the present disclosure provides a multicomponent ear implant assembly that provides an ability to project with or without a tissue expansion device. When used, the accompanying tissue expansion mechanism allows for calculated projection with gradual expansion and growth.

In variations where a multistage implantation process is contemplated, the first tissue scaffold component 62 may further comprise a removable guard 88 that serves to protect one or more edges of the implanted first tissue scaffold component 62. Thus, the removable guard 88 may cover and protect the edges of the rectangular projection of the second interlock member 84 during initial implantation in the patient. The removable guard 88 may be formed of a biocompatible material, such as silicone. However, the removable guard 88 is configured to be removed during a subsequent second procedure, when the second tissue scaffold component 80 is implanted into the patient. The removable guard may have a knob or other feature that facilitates removal by a surgeon. The removable guard 88 protects the edge from tissue growth and provides a clean and unobstructed edge so that the first tissue scaffold component 62 and the second tissue scaffold component 80 can couple with one another without obstruction or interference. Thus the removable guard 88 may be considered to be a silicone place holder in first stage tissue scaffold that provides a fresh edge upon removal and facilitates precise fit of subsequent stage scaffold module. It should be noted that any edge or surface of an implantable device in accordance with the present disclosure that may require protection during implantation can have a removable guard disposed thereon. Further, other shapes and sizes are contemplated from those shown in FIG. 4D.

Figure 5A:
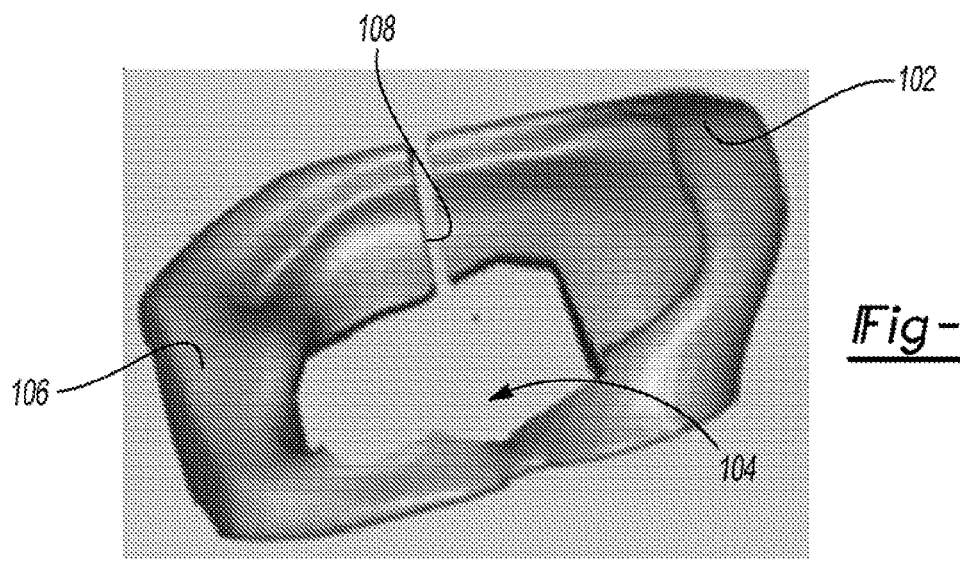
Figure 5B:
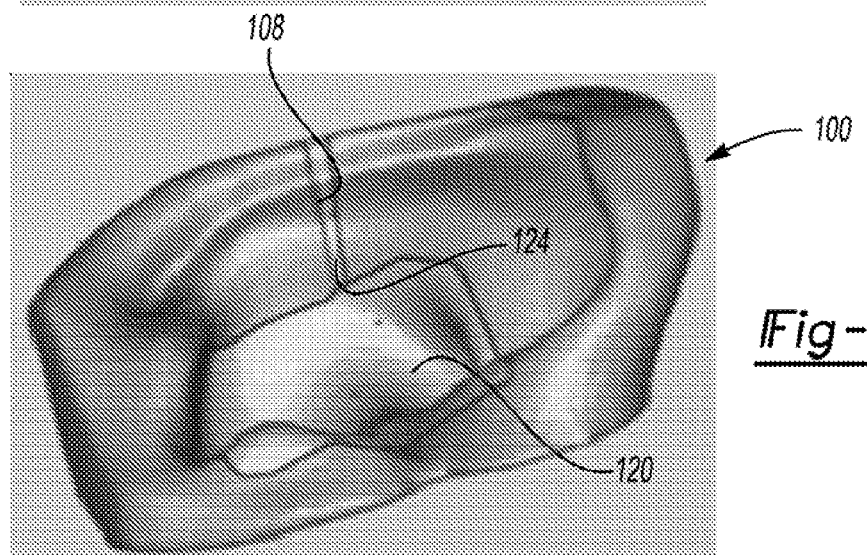
Figure 5C:
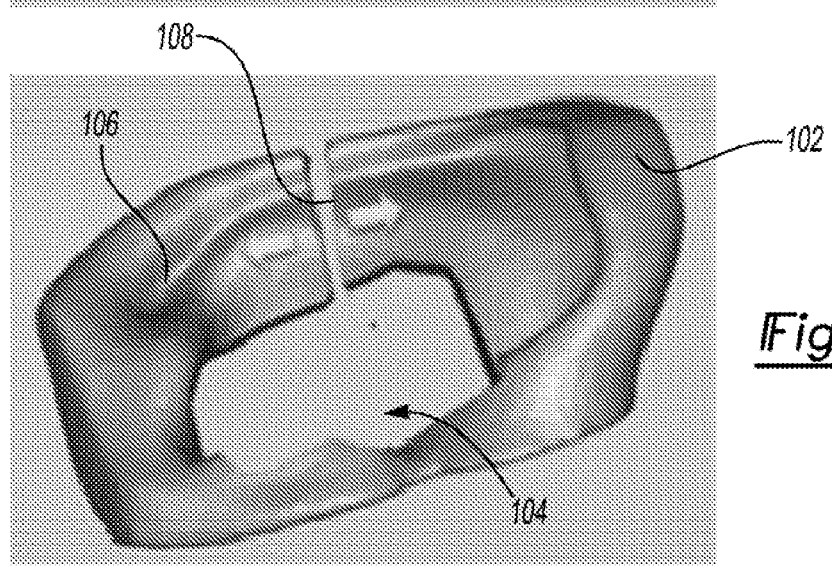

Referring to FIGS. 5A-5C, another multicomponent ear implant assembly 100 is shown that serves as a tissue scaffold when implanted in a patient (best seen in FIG. 5B). In FIG. 5A, the ear implant assembly 100 includes a first tissue scaffold component 102 that defines a central void region 104 and at least a portion of an outer ear framework 106 of the patient. The first tissue scaffold component 102 comprises a first biocompatible polymeric material having a first plurality of open pores (not shown in the models of FIGS. 5A-5C) configured to support cell growth. The first plurality of open pores may have the dimensions and properties described previously above. The first tissue scaffold component 102 further comprises at least one expandable opening 108. The expandable opening 108 may serve as a first interlock member. As shown in FIG. 5C, the expandable opening 108 expands the body of the scaffold corresponding to the body of the outer ear framework 106 outwards in the direction of the arrows.

The multicomponent ear implant assembly 100 also includes a second tissue scaffold component 120 that defines a base portion of the assembly 100 as shown in FIG. 5B. After implantation into the patient, the second tissue scaffold component 120 seats within a portion of the central void region 104 of the first tissue scaffold component 102, so that the second tissue scaffold component 120 is secured to the first tissue scaffold component 102. The second tissue scaffold component 120 comprises a second biocompatible polymeric material having a second plurality of open pores configured to support cell growth. The second plurality of open pores can have the same properties as discussed above. The second tissue scaffold component 120 further comprises a second interlock member 124. The second interlock member 124 may be in a shape of a rectangular projection that is dimensioned to fit within the expandable opening 108 of the first tissue scaffold component 102. Notably, other shapes complementary with the opposing interlock member are also contemplated. The expandable opening 108 on the first tissue scaffold component 102 and the second interlock member 124 on the second tissue scaffold component 120 are coupled together, as shown in FIG. 5B. Other interlock features may also be used, including those described previously above. Notably, the presence of the second tissue scaffold component 120 seated within the void region 104 of the first tissue scaffold component 102 forces the outer ear framework 106 outwards.

In certain aspects, a multicomponent ear implant assembly 100 like that shown in FIGS. 5A-5C may be used in a multistage implantation procedure. In certain variations, the first tissue scaffold component 102 may first be implanted in the patient to facilitate ingrowth of cells and tissue over and within the scaffold to define an outer ear framework. After a sufficient amount of tissue growth has occurred, then a second surgical procedure may implant the second tissue scaffold component 120 into the patient. The second tissue scaffold component 120 is seated within the void region 104 and the second interlock member 124 is disposed within the expandable opening 108 of the outer ear framework 106, serving to couple the first tissue scaffold component 102 to the second tissue scaffold component 120 during the procedure. Notably, the design of the ear implant shown in FIGS. 5A-5C uses the second tissue scaffold component 120 to expand the outer ear framework 106 of the first tissue scaffold component 102 as a "table leaf insert" and can also elevate the entire implant assembly 100. In this manner, the introduction of the second tissue scaffold component 120 serves to expand the first tissue scaffold component 102 and optionally raise a height and profile of the implant assembly 100, thus facilitating profiling to approximate natural ear shape in the second stage of growth within the tissue scaffold. Such a multistage implantation procedure may be particularly advantageous where the ear size may change (for example, in a growing child) or where the tissue at the target site is too thin or delicate to accommodate the height of the entire assembly in a single implantation procedure. In certain aspects, the second tissue scaffold component 120 can be subsequently replaced with a longer table leaf to further facilitate expansion and growth. In alternative aspects, the components of the multicomponent ear implant assembly 100 may be secured prior to an initial implantation surgery and implanted as an entire assembly in one procedure.

Thus, a two staged 3D printed ear scaffold implantation process can allow for improved outcomes and decreased complications when compared to a single staged implant for animal implantation. Without being limited to any particular theory, the hypothesis is that a two staged scaffold design allows for more robust tissue ingrowth and vascularization of the superficial ear scaffold, which upon elevation in the second stage will mitigate extrusion, infection, and scaffold exposure observed in single stage scaffold implants. Ear scaffold implants having a mechanism of modular scaffold expansion are thus contemplated. Such scaffolds provide the ability to predictably enlarge the ear scaffold at a second stage surgery, while simultaneously providing ear projection. The ability to provide for expansion of an ear framework is not presently possible, and is a unique design capability imparted by 3D printing of the scaffold implant assemblies prepared in accordance with certain aspects of the present disclosure.

In this embodiment, the mechanism of expansion emulates expansion provided by a table center leaf, with precision of increase in dimension and interlocking mechanism provided by the precision of the 3D printing design and process. The result of this design provides a novel feature to ear reconstruction—earlier implantation and the appearance of ear growth commensurate with growth of the child. Moreover, due to the unique nature of patient specific, 3D printed scaffolds allow for unparalleled control and match to the contralateral ear at both the initial framework implantation, and second stage elevation. 3D printed modular scaffolds can consistently increase ear scaffold dimension in the second stage surgery, giving the appearance of growth after the first stage surgery by at least about 20%.

Figure 6:
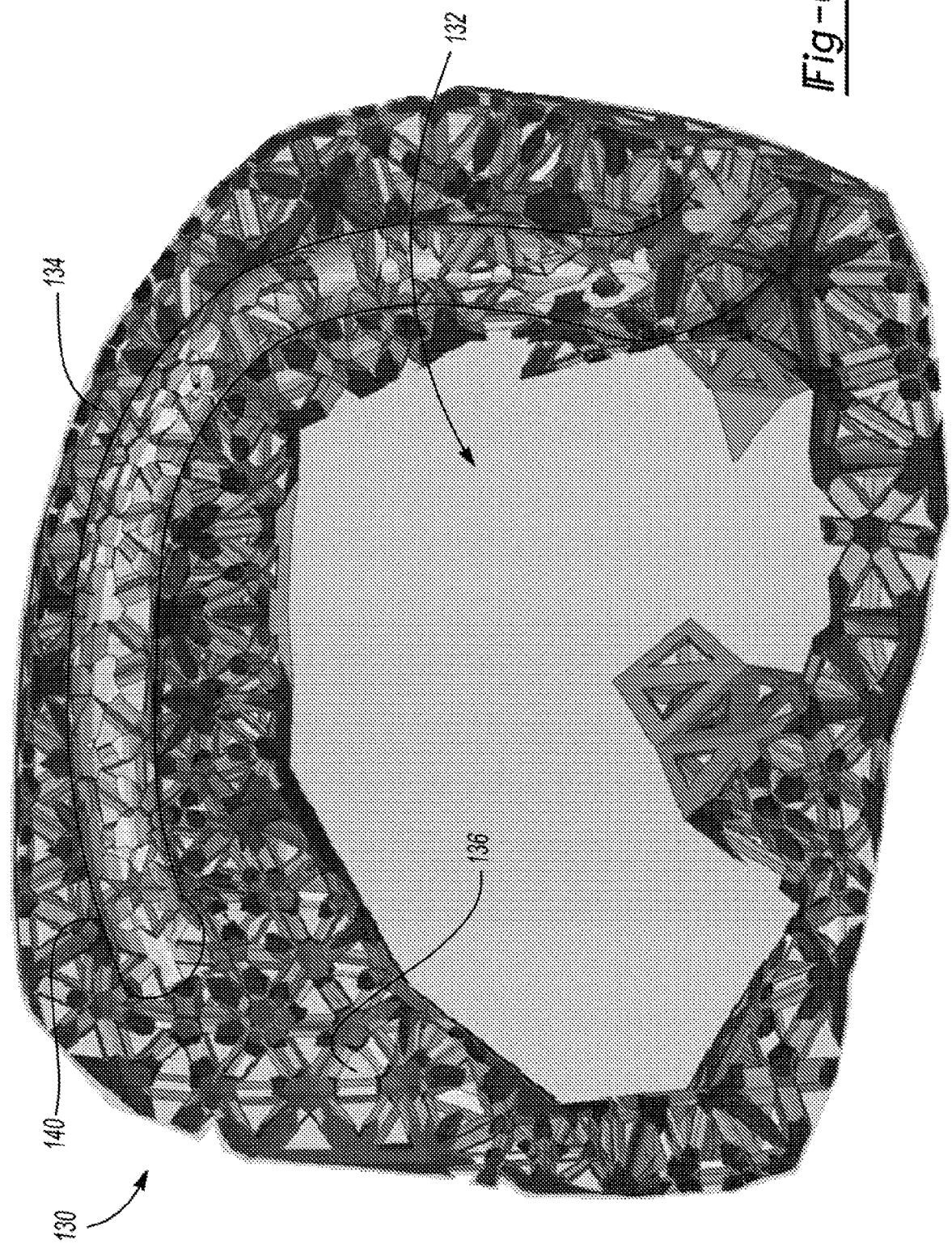
FIG. 6 shows a perspective top view of a first tissue scaffold component of a multicomponent assembly ear implant tissue scaffold device prepared in accordance with certain aspects of the present disclosure having an internal open channel disposed therein.
Figure 7:
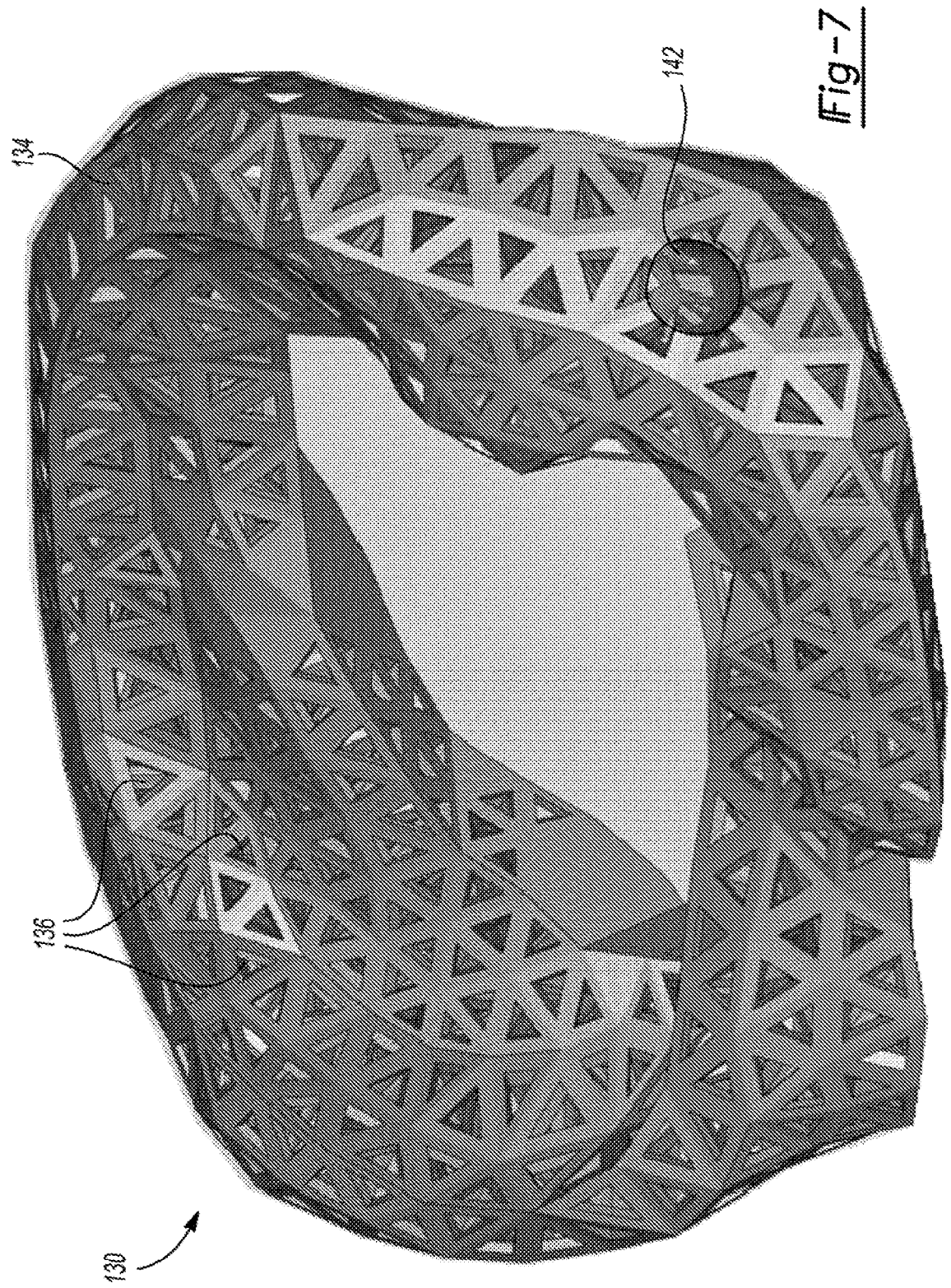
FIG. 7 shows a perspective lower view of the first tissue scaffold component in FIG. 6 showing a drain port opening.

FIGS. 6 and 7 show a first tissue scaffold component 130 that defines a central region 132 and an outer ear framework 134 of a patient. To the extent that the features of the first tissue scaffold component 130 are the same as the previous embodiments described, for brevity, they will not be repeated herein. The first tissue scaffold component 130 comprises a plurality of open pores 136 configured to support cell growth and having a tetrahedral unit shape with dimensions and properties previously described. An internal open channel 140 is disposed within the first tissue scaffold component 130 and is in fluid communication with the plurality of pores 136. As best seen in FIG. 7, the first tissue scaffold component 130 includes a drain port 142 that is in fluid communication with the internal open channel 140. In this manner, in certain variations, an external suction device, such as a conduit having negative pressure, can be attached to the drain port 142 to facilitate removal of fluids from the internal open channel 140 and pores 136 as needed. Suction pathways allow the scaffold implant to serve as its own suction port, thus providing optimal soft tissue adherence and minimization of hematoma or seroma formation.

In certain other variations like that in FIG. 14, a multi-component ear implant assembly 150 includes both a first tissue scaffold component 152 that defines a central void region 154 and at least a portion of an outer ear framework 156 of a patient and a second tissue scaffold component 160 that defines a body portion and seats within the central void region 154 of the first tissue scaffold 152. Both the first tissue scaffold component 152 and the second tissue scaffold component 160 may comprise biocompatible polymeric materials and have a plurality of open pores configured to support cell growth. The first tissue scaffold component 152, the second tissue scaffold component 160, or both may include one or more hollow features 170 through a body of the scaffold. The hollow feature(s) 170 are configured to receive a tissue sample. In certain variations, the hollow feature(s) 170 is cylindrical with a round or circular cross-section, although other shapes including semilunar, elliptical, and the like are contemplated. The hollow feature may have a width or diameter of greater than or equal to about 1 mm to less than or equal to about 12 mm. In various aspects, the hollow feature is significantly larger than a plurality of pores in the scaffold, for example, an average width or diameter of the hollow feature may be at least 100% greater than an average dimeter pore size. The hollow feature may extend from one surface into the scaffold for a predetermined distance or may fully extend from one surface through an opposite surface to form an aperture through the scaffold. In certain embodiments, the hollow feature may be designed with back stop rim or ledge that prevents displacement of the tissue sample during handling and implantation into the patient. As shown in FIG. 14, the hollow features 170 include a first plurality of hollow features 172 in the first tissue scaffold component 152 having a first diameter. The hollow features 170 also include a second plurality of hollow features 174 in the second tissue scaffold component 160 that have a second diameter. The first diameter and second diameter are distinct from one another. As shown, the second diameter is greater than the first diameter.

One or more tissue samples may be harvested from the patient (or from another source of tissue) via a punch biopsy tool or other technique. The punch biopsy tool may be dimensioned to provide tissue samples that will seat within the hollow feature. In certain variations, the tissue harvested is cartilage tissue. After harvesting, the tissue sample may be disposed within the hollow features of the scaffold implant. Thus, the scaffold implant may be seeded by implanting cartilage punches prior to implantation into the patient. Custom punch biopsy designs and accompanying scaffold inserts allow for rapid and precise harvest and distribution of tissue within the scaffold when the tissue sample is disposed in the one or more hollow features. The scaffold design allows for precise placement and distribution of cartilage punches. In certain variations, a plurality of hollow features may be provided in various regions of the first tissue scaffold component and/or the second tissue scaffold component. The size and distribution of hollow features for accepting cartilage punch biopsy inserts can be determined based on Finite Element Analysis to guide relief of overlying soft tissue strain and vascular compromise. In certain variations, the hollow features that accept prefabricated inserts are offset, so as to allow the tissue sample to protrude from the tissue scaffold, ranging from greater than or equal to about 50 μm to less than or equal to about 10 mm, based on Finite Element Analysis guiding relief of overlying soft tissue strain and vascular compromise. Porous scaffold designs radiating from prefabricated hollow features that accept punch biopsy inserts facilitate cellular, paracrine, and autogenous growth factor dissemination. Further, an eluting peri-insert component allows for gradual dissolution of the tissue sample/cartilage punch, further facilitating cellular outgrowth, paracrine influence. Thus, a macropore hollow feature configured to accept cartilage punches advantageously promotes cellularization of the tissue scaffold, while minimizing operative time and accelerating translation.

In yet other variations, a multicomponent ear implant assembly includes both a first tissue scaffold component that defines a central void region and at least a portion of an outer ear framework of a patient and a second tissue scaffold component that defines a body portion and seats within the central void region of the first tissue scaffold. Both the first tissue scaffold component and the second tissue scaffold component may comprise biocompatible polymeric materials and have a plurality of open pores configured to support cell growth. The first tissue scaffold component, the second tissue scaffold component, or both may include at least one Luer connector. The Luer connector is compatible with a complementary Luer connector, for example, on a syringe to form a Luer lock providing a fluid seal. The Luer connector may be in fluid communication with the plurality of pores. Optionally, one or more internal channels may also be disposed within the first tissue scaffold component and/or the second tissue scaffold component and in fluid communication with the Luer connector. A Luer connector can form a Luer lock assembly with an external syringe or injector, allowing for external materials to be injected within the pores or hollow features within the implant scaffold. For example, hydrogels, solutions, nanoparticles, growth factors, cells, tissue infusions, and the like may be injected into the ear implant device via the Luer lock.

In certain variations, an implant assembly for reconstruction of auricular tissue in a patient is provided, where the implant comprises a first tissue scaffold component and a second tissue scaffold component. The first tissue scaffold component comprises a first biocompatible polymeric material having a first plurality of open pores configured to support cell growth. The first tissue scaffold component defines a central void region and at least a portion of an outer ear framework of the patient after implantation. The second tissue scaffold component comprises a second biocompatible polymeric material having a second plurality of open pores configured to support cell growth. The second tissue scaffold component defines a base portion and after implantation into the patient. The second tissue scaffold component seats within the central void region of the first tissue scaffold component, so that the second tissue scaffold component is secured to the first tissue scaffold component.

In certain embodiments, the first plurality of open pores in the first tissue scaffold component has a first pore density in a first region. The pore density thus translates to a first rigidity level. The first tissue scaffold component also has a second region having a second pore density distinct from the first pore density. The second pore density thus relates to the second region having a second rigidity level distinct from the first rigidity level. Alternatively or in addition, the second plurality of open pores in the second tissue scaffold component may have a first pore density in a first region having a first rigidity level, while the second tissue scaffold component has a second pore density distinct from the first pore density in a second region. The second region thus has a second rigidity level distinct from the first rigidity level. In this manner, the implant devices have a tailored scaffold porosity, which provides the capability of forming hybrid or gradated scaffold pores within the ear scaffold implant. The pore density and/or pore architecture imparts strength and rigidity in desired regions of the implant, for example, at foundational subunits (e.g., concha cymba, and concha cavum regions of the ear). Similarly, the pore density and/or porous architecture can impart flexibility in desired regions of the implant, for example, at foundational subunits adjacent to soft tissue interfaces (e.g., helix, antihelix, and intertragal complex regions of the ear). Thus, the implant scaffold stiffness can be mediated by microstructure design, providing the ability to finely balance a construct design that is robust enough to prevent contracture, yet with a modulus low enough to reduce the risk of mechanical strain on vasculature with subsequent construct extrusion through overlying soft tissue.

In certain aspects, differences in porosity within the tissue implant can desirably impart gradated permeability to facilitate fluid flow within the pores of the implant in a predetermined direction. Moreover, controlling the porous characteristics of the tissue scaffolds can influence differentiation of pluoripotent stem cells, which is believed to provide an optimal environment for cartilage or bone. Thus, the pores may have different sizes and pore density or different shapes within the scaffold implant design from one region to another. High internal permeability and low peripheral permeability allow for low impedance and high homogeneity with external materials introduced into the implant, such as hydrogels, solutions, nanoparticles, growths factors, cells, tissue infusions, and any combinations thereof.

In other variations, the first tissue scaffold component may have an average porosity level that is distinct from an average porosity level in the second tissue scaffold, which may provide different levels of rigidity and/or flexibility in the first tissue scaffold component as compared to the second tissue scaffold component. The first plurality of open pores in the first tissue scaffold component may thus have a first average pore density corresponding to a first average rigidity level. The second plurality of open pores in the second tissue scaffold component has a second average pore density corresponding to a second average rigidity level distinct from the first average rigidity level. In certain variations, the second average rigidity level in the second tissue scaffold is greater than the first average rigidity level in the first tissue scaffold, so that the first tissue scaffold component has higher flexibility. The second tissue scaffold component having a higher rigidity in the central region of the implant provides structural support to the auricular tissue as it regrows and helps to facilitate projection and expansion, while minimizing or preventing collapse of the reconstructed tissue.

In certain aspects, the auricular reconstruction scaffold implants prepared in accordance with the present disclosure provides one or more of the following benefits: (1) ease and precision to reconstruct complex ear geometry, (2) personalization to replicate an individual's auricular anatomic structure with the ability of expansion giving the appearance of growth, (3) resistance to contraction, for example, allowing meticulous control of mechanical properties, specifically, to impart sufficient stiffness allowing resistance against contracture, while balancing compliance to prevent dehiscence, (4) preventing exposure due to dehiscence with subsequent infection, (5) potential to serve as a platform to deliver biologics for tissue growth, (6) customization to implement different staged procedures and special surgical requirements such as surgical drains, and (7) facilitating tissue engineering in a low cost, low resource environment.

In certain variations, the present disclosure contemplates a kit that may have a plurality of distinct implant assemblies formed in accordance with the present teachings as described in the various embodiments above. Each ear implant device may be prefabricated with a range of certain predetermined properties, such as size, rigidity/flexibility, and the like or with different features, such as internal channels, drain ports for suction and draining, hollow regions for receiving tissue samples, Luer connectors, implants formed from resorbable biocompatible materials or non-resorbable biocompatible materials, bioactive agents or biomaterials, and the like. For example, such implant assemblies in the kit may have different dimensions or sizes to provide a variety of options of available ear implants, so that the medical practitioner can select an appropriately sized ear implant for the specific patient. In one aspect, the present disclosure contemplates a kit comprising at least one implant assembly having a first size and at least one implant assembly having a second size distinct from the first size. The kit may include other components, such as tools like a tissue harvesting tool (e.g., one or more punch biopsy tools), a syringe that may interface with a Luer connector on the implant to form Luer lock, and the like.

In certain other variations, a method for reconstructing auricular tissue in a patient is provided. The method may include implanting a first tissue scaffold component in an ear region of the patient. The first tissue scaffold component comprises a first biocompatible polymeric material having a first plurality of open pores that support cell growth after the implanting. The first tissue scaffold component defines a central void region configured to receive a second tissue scaffold component and at least a portion of an outer ear framework of the patient. The second tissue scaffold component seats within the central void region of the first tissue scaffold component and defines a base portion of an implant assembly comprising the first tissue scaffold component and the second tissue scaffold component.

In certain variations, the implanting may be a first implanting and after auricular tissue has grown over the first tissue scaffold component in the patient, the method further comprises a second implanting of the second tissue scaffold component in the central void region to secure the second tissue scaffold component to the first tissue scaffold component. The second tissue scaffold component comprises a second biocompatible polymeric material having a second plurality of open pores that support cell growth and increases an elevation of the implant assembly.

In other variations, the first tissue scaffold component further comprises a removable guard to protect at least one edge of the first tissue scaffold component and prior to the second implanting of the second tissue scaffold, the removable guard is removed.

In yet other variations, the first tissue scaffold component further comprises a first interlock member and the second tissue scaffold component further comprises a second interlock member. The first interlock member and the second interlock member are coupled together to secure the first tissue scaffold component to the second tissue scaffold component and the first interlock member and the second interlock member together define a dove tail interlock assembly or an offset snap assembly.

In certain variations, at least one of the first tissue scaffold component or the second tissue scaffold component further comprises at least one hollow feature configured to receive a tissue sample. The method includes harvesting the tissue sample from the patient and inserting it into the at least one hollow feature prior to the first implanting, the second implanting, or both the first implanting and the second implanting.

In certain other variations, the first tissue scaffold component comprises at least one expandable opening and the second tissue scaffold component seats with the central void region to facilitate outward expansion of the first tissue scaffold component after the second implanting of the second tissue scaffold component in the patient.

In yet other variations, the second tissue scaffold component comprises a rectangular projection and the first tissue scaffold component defines a rectangular void to receive the rectangular projection, wherein the rectangular projection is configured to elevate the implant assembly.

In further variations, the rectangular projection comprises a tissue expansion device and the method further comprises expanding tissue by adjusting the tissue expansion device.

In certain variations, the first tissue scaffold component further comprises a drain port and an internal channel in fluid communication therewith. The method further comprises connecting the drain port with a conduit under negative pressure to remove fluids within the internal channel.

Various embodiments of the inventive technology can be further understood by the specific examples contained herein. Specific Examples are provided for illustrative purposes of how to make and use the compositions, devices, and methods according to the present teachings and, unless explicitly stated otherwise, are not intended to be a representation that given embodiments of this invention have, or have not, been made or tested.

EXAMPLES

Example A

Scaffolds are created using image-based hierarchical design and laser sintering methods. The manufacturing methods begin with the possibility of using photographically or radiographically obtained patient specific imaging data to 3D print unique custom scaffolds, an improvement over prefabricated porous polyethylene implants. Furthermore, laser sintering allows for the ability to impart meticulous architecture of the pores within the already intricately designed scaffold.

Hierarchical image designs are created separately for the global ear structure. Designs are represented by a density distribution within a voxel format, similar to the way 3D images are represented by density distributions within a voxel dataset. Separate voxel design datasets are created for the anatomic structure, based on an actual patient radiologic data. Different pore structures are created by generating either periodic or random geometries—such as spheres or cylinders using density distributions in voxel data structures created by specially written MATLAB™ codes. Both the anatomic and porous designed voxel structures are then converted into a triangular surface .STL representation. A final scaffold design is created by mapping a porous architecture STL file into the appropriate location of the anatomic dataset (also represented as a .STL file after conversion in the commercial software MIMICS™ by Materialise). A porous architecture, either periodic spherical or random pores, is mapped into the global patient specific anatomic design for the ear or nose using Boolean intersection operations of the custom designed porous architecture .STL file and the ear .STL file using MIMICS to create the final scaffold design.

The manufacturing process utilizes laser sintered polycaprolactone (PCL), an FDA approved, resorbable biopolymer. An EOS P100 laser sintering system is used with powder size, bed temperature, and laser sintering power as described in Partee B., et al., "Selective laser sintering process optimization for layered manufacturing of CAPA 6501 Polycaprolactone Bone Tissue Engineering Scaffolds," J. Manuf. Sci. E. 128:531-540 (2006), the relevant portions of which are hereby incorporated by reference, to fabricate patient specific ear scaffolds. A 69% scaled male left ear is utilized. Random porosity is set at 61%. Spherical porosity is set at 65%. Pore size is 2.5 mm.

In Vitro Cartilage Growth

Institutional Animal Care Committee protocol approval is obtained for the study in this example. Chondrocytes are isolated from freshly harvested porcine auricular cartilage. Care is taken to isolate cartilage while discarding overlying perichondrium. Minced cartilage fragments are digested with 0.2% type II collagenase (Worthington Biochemical, Lakeview, N.J.) for 16 hours in a 37° C., 5% $CO_2$ incubator with agitation. Digest is filtrated through a 70 micron mesh (Becton Dickenson, Franklin Lakes, N.J.), the cells are centrifuged to precipitate, then counted, and plated. The proliferation medium comprises of Ham's F-12 (Gibco, BRL/Life Technologies, Grand Island, N.Y.), with the addition of 10% fetal bovine serum (FBS, Sigma-Aldrich, St. Louis, Mo.), 5 mg/ml ascorbic acid, and an antibiotic/antimicotic solution containing 10,000 U/ml penicillin, 10 mg/ml streptomycin, and 25 μg/ml Fungizone.

Chondrocytes are seeded into the auricular PCL scaffolds using a type I collagen/hyaluronic acid composite gel. The gel solution includes type 1 collagen at a concentration of 6 mg/ml in acetic acid (Becton Dickinson, Frankin Lakes, N.J.) and hyaluronic acid at a concentration of 3 mg/ml (LifeCore Biomedical, Chaska, Minn.). Cells are rinsed with Hanks Buffered Saline Solution (HBSS, Gibco, BRL/Life Technologies, Grand Island, N.Y.), trypsinized (0.25% trypsin, Gibco), aliquoted into 15 ml conical tubes and placed on ice. Prior to seeding, the PCL scaffolds are placed in custom-designed SYLGARD™ silicone (Dow Corning, Midland, Mich.) molds to prevent leakage of the cell-collagen solution prior to gelation. After resuspending the cells in the collagen I gel solution, sodium bicarbonate is added, the cell suspension is carefully pipetted into the PCL scaffolds and the constructs are placed in an incubator (37° C., 5% $CO_2$) for 30 minutes for gelation to occur. Approximately $25 \times 10^6$ chondrocytes are utilized per scaffold. Seeded constructs are cultured in sterile, dynamic conditions with incubation at 37° C., 5% $CO_2$. The culture medium includes serum free F12 (Gibco), with the addition of 5 ng/ml TGF-β 2 (Pepro Tech, Rocky Hill, N.J.), ITS+premix (Becon Dickinson), 110 mm pyruvate (Gibco), 10 μm dexamethasone (Sigma), and 5 μg/ml ascorbic acid.

In Vivo Scaffold Implantation

NIH-Foxn1 strain 316, Charles River athymic rodents, 7-10 weeks of age, are implanted with seeded ear scaffolds after 4 weeks of in vitro culture. General anesthetic is administered. A dorsal incision is performed with development of subcutaneous pocket. Layered skin closure is performed with 4-0 monocryl subcuticular closure.

After 9.5 weeks, ear constructs are histologically analyzed. For histology, 1 random and 1 spherical ear scaffold is divided in to quarters. The specimens are fixed with 10% phosphate buffered formalin for 24 h, and then embedded in paraffin and sectioned using standard histochemical techniques. Serial slide sections are stained with hematoxylin and eosin or Safranin O.

Auricular constructs with two micropore architectures, random and spherical, are rapidly manufactured with high fidelity anatomic appearance as shown in FIGS. 8A-8D. FIG. 8A shows a randomly distributed pore architecture, while FIG. 8B shows a regularly distributed pattern of spherical pores in the tissue implant. FIG. 8C shows the PCL scaffold placed in a custom-designed SYLGARD™ silicone (Dow Corning, Midland, Mich.) mold to prevent leakage of a cell-collagen solution prior to gelation. FIG. 8D shows the PCL scaffold after gelation of the cell-collagen solution on the surface.

Subcutaneous implantation of the scaffolds results in excellent external appearance of both anterior and posterior auricular surfaces, as shown in FIGS. 9A-9C. Scaffold landmarks including helix, antihelix, conchal bowl, tragus, antitragus, and intertragal incisor are readily evident after subcutaneous implantation (FIGS. 9A-9B). Projection is approximately 25-30° off horizontal plane of the animal dorsum (FIG. 9C).

Histologic analysis displays more robust Safranin O staining for the spherical pore scaffolds in comparison to random pore scaffolds as shown in FIGS. 10A and 10B. FIG. 10A shows Safranin O staining for the random pore architecture scaffold, while FIG. 10B shows Safranin O staining for the spherical pore structure. The posterior surface up on right dorsum, anterior surface up on left dorsum (left). Anterior face surface details (right upper) and anterior oblique view highlighting projection (right lower). Cartilage growth is seen both in the peripheral and central aspects of the auricular scaffolds. The cartilage growth is much greater for the spherical pore architecture, as shown in FIG. 10B. Growth is observed adjacent to polycaprolactone structure though did not extend beyond the confines of the scaffold as shown in FIGS. 10A-10B. H and E staining additionally had more apparent cartilage matrix present in the spherical scaffolds.

This example further elucidates the potential benefit of various pore designs. Previous work demonstrated the ability to direct pluripotent bone marrow derived stem cells toward either an osteocyte or chondrocyte differentiation by adjusting pore design. Here, 3D printed ear scaffolds are rapidly and consistently produced from bioresorbable polycaprolactone. Though aesthetic appearance is not a primary goal of this example, the ear scaffolds reveal excellent detail when subcutaneously implanted. Appearance is believed to be further improved with use of negative pressure vacuum suction.

Cartilage growth is observed in both scaffold designs in FIGS. 10A and 10B, but appears to be more robust in the "chondrogenic" spherical pore design. Furthermore, cartilage growth appears to be equally in the peripheral and central component of the scaffolds, though does not appear to grow beyond the boundaries of the scaffold. Therefore, creation of spherical micropores within the scaffold architecture appears to impart greater chondrogenicity of the scaffold, although both types of pores promote cell growth in the scaffold.

Example B

This example explores a role of cellular population of 3D printed ear scaffolds as compared to unseeded 3D printed scaffolds. This example establishes the upper (resorbable 3D printed scaffold with seeded cells) and lower bounds (3D printed resorbable scaffold alone) of ear reconstruction using tissue engineering. Without being limited to any particular theory, the theoretic optimal biologic scenario is believed to have the ear scaffold maximally seeded with a chondrocyte embedded hydrogel. In this scenario, the goal of an ear scaffold is to become confluent with ear cartilage. The theoretic optimal translational scenario—by avoiding regulatory demands brought by using cell therapy—is utilizing an unseeded scaffold and inducing nearby cellular ingrowth. It is believed that while both tissue scaffolds with predefined tetrahedral pores, seeded with chondrocyte embedding hydrogels and unseeded, will avoid distortion or contraction, the seeded scaffolds will exhibit improved soft tissue coverage and have lower exposure and fracture rates.

Cell seeding of scaffold implants can be difficult to be able to harvest an adequate number of primary chondrocytes. Estimates of about 100 t to about 150 million cells are believed to be likely needed to engineer cartilage of human ear shape and volume. Preliminary data described herein supports use of co-culture of primary chondrocytes with adipose derived stem cells (ADSC).

Microporous PCL scaffolds are seeded with porcine ADSCs and chondrocytes in experimental ratios of 1:1, 2:1, 5:1, and 10:1. Scaffolds are seeded with cells encapsulated in a hyaluronic acid/collagen hydrogel and cultured for 4 weeks without chondrogenic growth factors. Subcutaneous in vivo implantation of scaffolds is performed in an athymic rat model. NIH-Foxn1 strain 316, Charles River, 7-10 weeks of age rodent for an animal model provides an excellent match to pediatric skin quality and thickness. Scaffolds are explanted after 4 weeks for histologic and biochemical analysis. Histologic demonstration of cartilage growth is seen in all experimental groups. One-way ANOVA analysis demonstrated no significant difference in sulfated glycosaminoglycan (sGAG)/wet weight (ug/mg) concentration levels for 1:1, 2:1, and 5:1 experimental groups [$F_{(2, 15)}$=0.028, $\alpha$=0.05, p=0.97].

Immunohistochemistry demonstrates generous type II collagen deposition in all experimental groups is shown in FIG. 11.

Both methods, seeding with chondrocytes alone or in co-culture with ADSCs, meet the criteria for near term clinical translation. Both methods allow for autologous cell sources with harvest and seeding at the time of scaffold implantation in the operating room.

Example C

This example is for determining the viability of utilizing a combination of adipose-derived stem cell-chondrocyte co-culture and three-dimensional (3D) printing to produce 3D bioscaffolds for cartilage tissue engineering. A feasibility study for cartilage tissue engineering with in vitro and in vivo animal data is described herein. Co-culture, where chondrocytes and mesenchymal stem cells (MSCs) are simultaneously seeded onto tissue engineering scaffolds, is used herein. Here the use of a co-culture model using adipose-derived stem cells (ASCs) and chondrocytes for cartilage tissue engineering (CTE) in conjunction with the inventive ear implant scaffolds. The co-culture technique can be adapted for craniofacial cartilage applications using hydrogels combined with 3D-printed bioresorbable scaffolds and that a variety of ratios of ASCs-to-chondrocytes may be utilized. This approach affords the potential for patient-specific CTE using computer-sided design (CAD) while mitigating the limitations of cell availability and need for prolonged in vitro cell culture or exogenous growth factor exposure of traditional CTE approaches.

Protocol approval is obtained by the University of Michigan Institutional Animal Care & Use Committee and the University of Illinois Institutional Animal Care & Use Committee (University of Michigan #3857, University of Illinois #10114).

Scaffold Design and Manufacturing Via 3D Printing

Scaffolds are created using previously described image-based hierarchical design methods discussed above. This process can be used to create patient-specific tissue engineering scaffolds of any geometry. A standard 10 mm×5 mm cylindrical disc scaffold macroarchitecture with a 2.7 mm spherical pore internal microarchitecture is chosen for this study to produce consistency of constructs for tissue analysis (FIG. 2A). This yields an overall scaffold porosity of 68.3% with an available volume per scaffold of 268 µL. A midline groove is incorporated into the scaffold to facilitate bifurcation during analysis. The final scaffold design is then 3D printed using an EOS P100 laser sintering system (EOS North America, Novi, Mich.) adapted to laser sinter L-polycaprolactone (PCL) powder (PCL Source: Polysciences, Warrington, Pa.; PCL Preparation: Jet Pulverizer, Moorsetown, N.J.). The laser sintering process can accurately reproduce feature sizes on the order of 70 µm and produce over 500 representative scaffolds with a single print cycle. Scaffolds are cleaned of residual excess powder via sonication in 70% sterile ethanol then sterilized in a 24 hour 70% sterile ethanol soak prior to use.

Cell Harvest and Culture

Porcine ASCs derived from subcutaneous back fat and chondrocytes derived from auricular and tracheal cartilage are harvested from adolescent Yorkshire pigs using the methods previously developed by Wheeler and colleagues. Primary (P0) ASC and chondrocyte cells are spun down and frozen prior to cell seeding experiments. At the time of preparation for scaffold seeding, cells are thawed and expanded in growth media comprising of high-glucose Dulbecco's Modified Eagle's Medium (DMEM) (Gibco) with 10% fetal bovine serum (FBS) (Gibco), 1% pen/strep, and 0.2% Fungizone in a 37° C., 5% $CO_2$ incubator. ASCs are expanded to passage 2 (P2) and chondrocytes expanded to passage 1 (P1) to provide sufficient cells for seeding. Cells are passaged at 90% confluence.

Creation of Experimental Ratios and Scaffold Seeding

Porcine adipose-derived stem cells and chondrocytes are isolated and co-seeded at 1:1, 2:1, 5:1, 10:1, and 0:1 experimental ratios in a hyaluronic acid/collagen hydrogel in the pores of 3D-printed polycaprolactone scaffolds to form 3D bioscaffolds for cartilage tissue engineering. Bioscaffolds are cultured in vitro without growth factors for 4 weeks then implanted into the subcutaneous tissue of athymic rats for an additional 4 weeks before sacrifice. Bioscaffolds are subjected to histologic, immunohistochemical, and biochemical analysis.

More specifically, adipose-derived stem cells and chondrocytes are rinsed with Hank's buffered saline solution (HBSS) (Gibco), trypsinized (0.25% trypsin) (Gibco), and aliquoted into experimental ratios of 1:1, 2:1, 5:1, 10:1, and 0:1 ASC-to-chondrocyte. Given that the cells are harvested from several animals, each cell type is pooled prior to creation of experimental ratios. Each experimental group is then re-suspended in a type I collagen:hyaluronic acid hydrogel solution and seeded into a prewet cylindrical PCL scaffold. The hydrogel comprises of type I collagen at a concentration of 6 mg/mL in acetic acid (Discovery Labware) and hyaluronic acid at a concentration of 3 mg/mL (LifeCore Biomedical). Prior to seeding, the PCL scaffolds are placed in custom-fabricated silicone (SYLGARD™, Dow Corning) molds to prevent extravasation of the seeding solution prior to gelation. A 0.05N NaOH in $NaCO_3$ solution is used to induce gelation and scaffolds are subsequently transferred to 24-well low attachment plates (Fischer Scientific) for culture. The cell seeding density is $2 \times 10^6$ cells/$cm^3$ and total of 12 scaffolds per experimental group are seeded.

In Vitro Culture

Seeded constructs are cultured in a sterile 37° C., 5% $CO_2$ incubator with agitation. Culture media comprises low-glucose DMEM with 10% FBS, 1% pen/strep, and 0.2% Fungizone and is changed every 2-3 days. After 4 weeks, six scaffolds from each experimental group are extracted for post-in vitro biochemical analysis, while the remaining six are reserved for in vivo implantation.

In Vivo Implantation

Seven athymic rats underwent implantation with tissue engineering scaffolds under general anesthesia with isoflurane delivered by mask. All scaffolds are rinsed with HBSS prior to implantation. All animals are male with each weighing between 250 and 305 g. Each animal is shaved, prepped with iodine solution after induction of anesthesia and a vertical incision is sharply made on the dorsum of the animal. A total of 4 scaffolds per animal are implanted in a subcutaneous pocket into randomized quadrants on the back of the animal. The incision is then closed with surgical staples, which are removed on post-operative day seven. After 4 weeks, the animals are euthanized and the scaffolds are harvested for post-in vivo analysis.

Biochemical Analysis

Post-in vitro and post-in vivo specimens are split along the midline groove to double the number of constructs for analysis. One-half of each construct is weighed wet, lyophilized, reweighed dry, and digested in 1 mg/mL Papain stock solution (Fischer Scientific) at 65° C. for 16 hours. PicoGreen assay (Invitrogen, Colecular Probes) is used to quantify the DNA content of the constructs with Lambda phage DNA (0-1 mg/mL) as a standard. The sulfated-glycosaminoglycan (s-GAG) content is measured using the Blyscan Glycosaminoglycan Assay (Accurate Chemical & Scientific Corp).

Histology and Immunhistochemistry

Remaining post-in vivo constructs are fixed in 4% formalin for 24 hours, embedded in paraffin (TissuePrep, Fischer Scientific), and processed using standard histologic procedures with a slice thickness of 10 μm. Stains included hematoxylin and eosin, Safrinin-O, and toluidine blue. Type II collagen immunohistochemical staining is performed using 5 μg/mL primary mouse anti-type II collagen monoclonal antibodies (Hybridoma, University of Iowa).

Statistical Analysis

Data for biochemical analysis (DNA and s-GAG expression) are collected from six samples after 4 weeks of in vitro cell culture and 4 weeks of in vivo growth. Data is expressed as mean±standard error of the mean (SEM). Results are analyzed using Student's t-test using SPSS 17.0 (SPSS Inc., Chicago, Ill.) and statistical significance is set to 5% ($\alpha = 0.05$) in all analyses.

Successful production of cartilage is achieved using a co-culture model of adipose-derived stem cells and chondrocytes, without the use of exogenous growth factors. Histology demonstrates cartilage growth for all experimental ratios at the post-in vivo time point confirmed with type II collagen immunohistochemistry. There is no difference in sulfated-glycosaminoglycan production between experimental groups.

Tissue engineered cartilage is successfully produced on 3D-printed bioresorbable scaffolds using an adipose-derived stem cell and chondrocyte co-culture technique. This potentiates co-culture as a solution for several key barriers to a clinically-translatable cartilage tissue engineering process.

Thus, in vitro co-culture of porcine ASCs and chondrocytes in 3D-printed PCL cylindrical discs with an internal spherical porous architecture results in growth and maintenance of cartilage-like tissue after 8 weeks. Surgical implantation is straightforward and the scaffolds are well tolerated by the animals with no minor or major complications. There is good maintenance of structural support by the PCL scaffolds after 4 weeks growth in a subcutaneous pocket as shown in FIG. 2B. Histologically normal appearing cartilage growth is noted in all experimental groups after 1 month of in vivo culture. The degree of histologic cartilage deposition is subjectively higher in the experimental co-culture groups compared to the control group of chondrocytes alone (FIG. 11), which is confirmed with type II collagen immunohistochemistry. In particular, the 5:1 ASC-to-chondrocyte ratio provided well delineated hyaline cartilage architecture in histology, with dense collagen deposition and lacunae surrounding the chrondrocytes and differentiated ASCs as shown in FIG. 12.

Biochemical analysis results are summarized in FIGS. 13A-13B. There is no statistically significant difference in DNA/wet weight (ng/mg) or s-GAG/wet weight (μg/mg) content between the co-culture experimental groups at the post-in vitro or post-in vivo time points. There is a statistically significant higher s-GAG content in all co-culture groups compared to the chondrocyte-alone control group (p<0.05 for all analyses) at the post-in vitro timepoint, however this difference disappeared at the post-in vivo timepoint.

Reconstruction of the auricular framework, whether performed in the setting of trauma, oncologic resection, or congenital malformation, are some of the most demanding procedures in facial reconstructive surgery. Tissue engineering holds several ubiquitous advantages, including the ability to create a patient-specific living construct using the patient's own cells. However, the primary limitation of utilizing solely chondrocytes for CTE is the large number of cells (up to $5 \times 10^7$) needed to seed human-sized craniofacial frameworks. The number of chondrocytes available from autologous cartilage is limited and passaging chondrocytes induces dedifferentiation with loss of type II collagen and sulfated glycosaminoglycan (s-GAG) production. Mesenchymal stem cells, of which ample cell quantities are available, have been posited as a solution to seeding requirements. Prior experiments have shown a variety of MSC types, including ASCs and bone-marrow stromal cells to be capable of chondrogenic differentiation. However, chondrogenic commitment of MSCs requires exogenous delivery of pro-chondrogenic growth factors (GFs) for weeks and cells can demonstrate a propensity for ossification.

Co-culturing of chondrocytes and MSCs is the technique described in this example can circumvent the limitations of utilizing chrondocytes or MSCs alone. In a co-culture model, chrondocytes and MSCs are simultaneously seeded onto a tissue engineering scaffold. Chondrocytes have been found to induce chondrogenic differentiation of the MSCs via production of exogenous GFs such as cytokine-like protein 1 (Cytl1), bone morphogenic protein-2 (BMP-2), parathyroid hormone-related peptide (PTHrP), and transforming growth factor-beta (TGF-β) as well as paracrine, juxtacrine, and gap-junction signaling pathways. In this way, chondrocytes maintain the chondrogenic niche required for commitment of MSCs to the chondrogenic phenotype, circumventing the need for exogenous GF delivery. Additionally, chondrocytes provide matrix for MSC migration and prevent ossification of MSC-derived chondrocytes.

The process of forming an ear tissue scaffold implant according to certain aspects of the present disclosure includes using CAD and 3D printing to produce high-fidelity patient-specific tissue engineering scaffolds using PCL, a bioresorbable polymer. Utilization of a bioresorbable material allows for eventual replacement of the scaffold with chondrocyte extracellular matrix, thus best emulating natural craniofacial cartilage. These scaffolds are then seeded with primary chondrocytes to produce tissue engineered auricular constructions. This process affords the ability to rapidly produce high-fidelity anatomic scaffolds while also allowing meticulous control of the pore microarchitecture.

ASC co-culture on 3D-printed tissue engineering scaffolds for successful CTE is believed to have been demonstrated for the first time. The use of ASCs with a co-culture technique is particularly advantageous for a clinically-translatable approach, given the low morbidity to harvest these cells compared to bone-marrow derived stromal cells. The described process can readily be adapted for tissue engineering constructs of any shape, including patient-specific auricular and nasal constructs using DICOM data The results demonstrate that all experimental ratios of ASC-to-chondrocytes result in chondrocytic differentiation of ASCs on short term in vivo analysis. Notably, chondrocytic commitment of the ASCs is achieved without the use of exogenous GFs during scaffold incubation. Using a cell count goal of $5 \times 10^7$ as the number of cells needed for a typical human-sized auricle, ratios of 10:1 and 5:1 ASC:PC yield cell number requirements which are clinically achievable from a cell harvest without the need to for prolonged passaging of cells in the laboratory setting. This represents important barriers to a clinically-translatable process for craniofacial CTE which appear to be overcome with a co-culture technique.

Interestingly, the co-culture scaffold groups all appear to perform similarly, despite different ratios of ASC-to-chondrocytes. Additionally, the co-culture groups appeared to outperform the chondrocyte-alone scaffolds, despite identical cell seeding densities. This may represent an inherent superior viability of co-cultured cells in this methodology or synergistic interaction of co-cultured cells to promote chondrogenesis. However, this could also be an artifact of decreased viability of chondrocytes in cell culture. Given that no analysis of cell viability or gene expression is performed in this example, these ideas are non-limiting and remain speculative.

This feasibility study is somewhat limited by a short in vivo incubation period and small number of implant constructs. As such, statistical differences of the biochemical characteristics of the experimental groups may have not been captured, as well as differences in the trajectory of tissue deposition with more prolonged in vivo growth. Given that the cells are seeded onto three-dimensional constructs, it is not possible to perform cell viability or gene expression analysis. However, PCL constructs prepared in accordance with certain aspects of the present disclosure are believed to be able to maintain construct fidelity for 2 to 3 years prior to resorption.

The present example thus provides the successful use of an ASC-chondrocyte co-culture technique and CAD-designed 3D-printed tissue engineering scaffolds for CTE in an animal model. This co-culture model produces formal cartilage production on short term in vivo follow-up in all experimental groups, including 5:1 and 10:1 ASC:chondrocyte ratios. The clinical availability of ASCs and lack of a need for prolonged exogenous GF exposure suggest this approach mitigates many of the limitations of traditional CTE approaches. These represent key barriers to the eventual goal of creating a clinically translatable patient-specific craniofacial CTE methodology that may be overcome using co-culture and 3D printing.

In various aspects, multiple tissue scaffold ear implant embodiments are described. The first is a single ear construct with the advantages of a single operative procedure providing a final reconstructive outcome. Recognizing this may induce undesirable mechanical strain on vascularity in the overlying soft tissue, a second version implements a multi-component tissue scaffold ear implant assembly. In certain embodiments, the implant assembly may include two distinct scaffold components that may have an interlock, such as a lock-in-key, dove tail design. Such an implant assembly provides the benefits of the meticulous anatomic fidelity in the first stage implant, followed by a seamless second stage elevation. This implant design is somewhat analogous to the Nagata surgical technique of auricular reconstruction. While adding a second operation, the potential benefit of a two stage implant is relief of soft tissue vascular strain and minimization of framework extrusion and exposures. Finally, a novel "leaf insert" design that would allow for calculated expansion of the framework in the second stage surgery, in concert with framework elevation, allows for the appearance of framework growth without necessitating cell therapy or growth factors.

The present disclosure thus contemplates methods that readily replicate any patient specific, complex auricular geometry, typically by mirroring the unaffected contralateral auricle. In addition, the ear implants (e.g., PCL implant) have sufficient mechanical stiffness to resist contraction and distortion. Importantly, the porous architecture can be designed to reduce the chance of dehiscence. The introduction of a modular design also provides the potential for early implantation in childhood and expansion of the ear scaffold in a subsequent stage surgery. A major limitation for implanting auricular devices in patients younger than 8 is matching growth of the contralateral ear. The ability to print a modular expandable ear would allow earlier auricular reconstructions. Modular expansion is a novel feature for an ear framework in ear reconstruction and is unique to the 3D printing processes. The scaffolds prepared in accordance with certain aspects of the present disclosure can potentiate a tissue engineering solution without needing the addition of cells, while also having the possibility to serve as a platform to deliver cells, tissue, and/or growth factors to regenerate cartilaginous structures.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An implant assembly for reconstruction of auricular tissue in a patient, the implant comprising:
   a first tissue scaffold component comprising a first biocompatible polymeric material having a plurality of open pores configured to support cell growth, wherein the first tissue scaffold component defines a central void region and is configured to define at least a portion of an outer ear framework of the patient after implantation; and
   a second tissue scaffold component comprising a second biocompatible polymeric material having a plurality of open pores configured to support cell growth, wherein the second tissue scaffold component defines a base portion and after implantation into the patient, the second tissue scaffold component seats within the central void region of the first tissue scaffold component, so that the second tissue scaffold component is secured to the first tissue scaffold component, wherein the second tissue scaffold component comprises a rectangular projection and the first tissue scaffold component defines a rectangular void to receive the rectangular projection, wherein the rectangular projection is configured to elevate the implant assembly, wherein the first tissue scaffold component further comprises a removable guard to protect one or more edges of the rectangular projection during initial implantation in the patient, wherein the removable guard is configured to be removed during a subsequent procedure when the second tissue scaffold component is implanted into the patient.

2. The implant assembly of claim 1, wherein the first tissue scaffold component further comprises a first interlock member and the second tissue scaffold component further comprises a second interlock member, wherein after implantation into the patient, the first interlock member and the second interlock member are coupled together to secure the first tissue scaffold component to the second tissue scaffold component.

3. The implant assembly of claim 2, wherein the first interlock member and the second interlock member together define a dove tail interlock assembly or an offset snap assembly.

4. The implant assembly of claim 1, wherein the first tissue scaffold component comprises at least one expandable opening and the second tissue scaffold component seats with the central void region to facilitate outward expansion of the first tissue scaffold component after implantation of the second tissue scaffold component in the patient.

5. The implant assembly of claim 1, wherein the first biocompatible polymeric material and the second biocompatible polymeric material respectively comprise polycaprolactone.

6. The implant assembly of claim 1, wherein at least one of the first biocompatible polymeric material or the second biocompatible polymeric material comprises a bioactive agent selected from the group consisting of: a cell adhesion factor, a growth factor, a peptide, a cytokine, a hormone, a pharmaceutical active, and combinations thereof.

7. The implant assembly of claim 1, further comprising a biomaterial selected from the group consisting of: an isolated tissue material, a hydrogel, acellularized dermis, an acellularized tissue matrix, a composite of acellularized dermis matrix and designed polymer, or a composite of acellularized tissue matrix and designed polymer, and combinations thereof.

8. The implant assembly of claim 1, wherein the first tissue scaffold component further comprises a drain port and an internal channel in fluid communication therewith.

9. The implant assembly of claim 1, wherein at least one of the first tissue scaffold component or the second tissue scaffold component further comprises at least one hollow feature configured to receive a tissue sample.

10. The implant assembly of claim 1, wherein the first tissue scaffold component further comprises a Luer lock in fluid communication with the plurality of pores.

11. The implant assembly of claim 1, wherein the plurality of open pores in the first tissue scaffold component has a first pore density in a first region and a first rigidity level and a second pore density distinct from the first pore density in a second region having a second rigidity level; or
   the plurality of open pores in the second tissue scaffold component has a first pore density in a first region having a first rigidity level and a second pore density distinct from the first pore density in a second region having a second rigidity level.

12. The implant assembly of claim 1, wherein the plurality of open pores in the first tissue scaffold component has a first average pore density corresponding to a first average rigidity level and the plurality of open pores in the second tissue scaffold component has a second average pore density corresponding a second average rigidity level distinct from the first average rigidity level.

13. The implant assembly of claim 1, wherein the first tissue scaffold component consists essentially of the first biocompatible polymeric material and an optional biomaterial and the second tissue scaffold component consists essentially of the biocompatible polymeric material and an optional biomaterial prior to implantation in the patient.

14. A kit comprising at least one implant assembly of claim 1 having a first size and at least one implant assembly of claim 1 having a second size distinct from the first size.

15. A method for reconstructing auricular tissue in a patient, the method comprising:

first implanting a first tissue scaffold component in an ear region of the patient, wherein the first tissue scaffold component comprises a first biocompatible polymeric material having a plurality of open pores that support cell growth after the implanting, wherein the first tissue scaffold component defines a central void region configured to receive a second tissue scaffold component and at least a portion of an outer ear framework of the patient, wherein the second tissue scaffold component seats within the central void region of the first tissue scaffold component and defines a base portion of an implant assembly comprising the first tissue scaffold component and the second tissue scaffold component;

after auricular tissue has grown over the first tissue scaffold component in the patient, implanting the second tissue scaffold component in the central void region to secure the second tissue scaffold component to the first tissue scaffold component, wherein the second tissue scaffold component comprises a second biocompatible polymeric material having a plurality of open pores that support cell growth, wherein the second tissue scaffold component comprises a rectangular projection and the first tissue scaffold component defines a rectangular void to receive the rectangular projection, wherein the rectangular projection is configured to elevate the implant assembly, wherein the first tissue scaffold component further comprises a removable guard to protect one or more edges of the rectangular projection during the first implanting in the patient, wherein the removable guard is removed before the implanting of the second tissue scaffold component in the patient.

16. An implant assembly for reconstruction of auricular tissue in a patient, the implant comprising:

a first tissue scaffold component comprising a first biocompatible polymeric material having a plurality of open pores configured to support cell growth, wherein the first tissue scaffold component defines a central void region and is configured to define at least a portion of an outer ear framework of the patient after implantation; and a second tissue scaffold component comprising a second biocompatible polymeric material having a plurality of open pores configured to support cell growth, wherein the second tissue scaffold component defines a base portion and after implantation into the patient, the second tissue scaffold component seats within the central void region of the first tissue scaffold component, so that the second tissue scaffold component is secured to the first tissue scaffold component, wherein the second tissue scaffold component comprises a rectangular projection and the first tissue scaffold component defines a rectangular void to receive the rectangular projection, wherein the rectangular projection comprises a tissue expansion device and is configured to elevate the implant assembly.

17. The implant assembly of claim 16, wherein the first tissue scaffold component further comprises a first interlock member and the second tissue scaffold component further comprises a second interlock member, wherein after implantation into the patient, the first interlock member and the second interlock member are coupled together to secure the first tissue scaffold component to the second tissue scaffold component, wherein the first interlock member and the second interlock member together define a dove tail interlock assembly or an offset snap assembly.

18. The implant assembly of claim 16, further comprising a biomaterial selected from the group consisting of: an isolated tissue material, a hydrogel, acellularized dermis, an acellularized tissue matrix, a composite of acellularized dermis matrix and designed polymer, or a composite of acellularized tissue matrix and designed polymer, and combinations thereof.

19. The implant assembly of claim 16, wherein at least one of the first tissue scaffold component or the second tissue scaffold component further comprises at least one hollow feature configured to receive a tissue sample.

20. The implant assembly of claim 16, wherein the plurality of open pores in the first tissue scaffold component has a first pore density in a first region and a first rigidity level and a second pore density distinct from the first pore density in a second region having a second rigidity level; or the plurality of open pores in the second tissue scaffold component has a first pore density in a first region having a first rigidity level and a second pore density distinct from the first pore density in a second region having a second rigidity level.

21. The implant assembly of claim 16, wherein the plurality of open pores in the first tissue scaffold component has a first average pore density corresponding to a first average rigidity level and the plurality of open pores in the second tissue scaffold component has a second average pore density corresponding a second average rigidity level distinct from the first average rigidity level.

* * * * *

UNITED STATES PATENT AND TRADEMARK OFFICE
CERTIFICATE OF CORRECTION

PATENT NO. : 11,564,792 B2
APPLICATION NO. : 16/608716
DATED : January 31, 2023
INVENTOR(S) : David A. Zopf et al.

It is certified that error appears in the above-identified patent and that said Letters Patent is hereby corrected as shown below:

In the Claims

Column 30, Claim 12, Line 57, after "corresponding", insert --to--.

Column 32, Claim 21, Line 47, after "corresponding", insert --to--.

Signed and Sealed this
Second Day of May, 2023

Katherine Kelly Vidal
Director of the United States Patent and Trademark Office